United States Patent [19]
Brown et al.

[11] Patent Number: 5,573,678
[45] Date of Patent: Nov. 12, 1996

[54] BLOOD PROCESSING SYSTEMS AND METHODS FOR COLLECTING MONO NUCLEAR CELLS

[75] Inventors: Richard I. Brown, Northbrook; Kyungyoon Min, Arlington Heights, both of Ill.

[73] Assignee: Baxter International Inc., Deerfield, Ill.

[21] Appl. No.: 472,750

[22] Filed: Jun. 7, 1995

Related U.S. Application Data

[63] Continuation-in-part of Ser. No. 814,403, Dec. 23, 1991, abandoned, and Ser. No. 748,244, Aug. 21, 1991, Pat. No. 5,322,620, which is a continuation of Ser. No. 514,995, May 26, 1989, Pat. No. 5,104,526, which is a continuation of Ser. No. 9,179, Jan. 30, 1987, Pat. No. 4,834,890.

[51] Int. Cl.⁶ ................................................ B01D 21/26
[52] U.S. Cl. .................. 210/782; 210/361; 210/369; 210/418; 210/424; 210/110; 210/112; 210/115; 494/3; 494/37; 604/410
[58] Field of Search ....................... 210/784, 782, 210/94, 787, 95, 361, 194, 369, 103, 104, 380.1, 110; 494/3, 710; 604/18, 37, 45, 416; 55/274, 407; 422/101

[56] References Cited

U.S. PATENT DOCUMENTS

| | | |
|---|---|---|
| 3,145,713 | 8/1964 | Latham, Jr. . |
| 3,519,201 | 7/1970 | Eisel et al. . |
| 3,655,123 | 4/1972 | Judson et al. . |
| 3,748,101 | 7/1973 | Jones et al. . |
| 3,957,197 | 5/1976 | Sartory et al. . |
| 4,007,871 | 2/1977 | Jones et al. . |
| 4,010,894 | 3/1977 | Kellogg et al. . |
| 4,094,461 | 6/1978 | Kellogg et al. . |
| 4,113,173 | 9/1978 | Lolachi . |
| 4,114,802 | 9/1978 | Brown et al. . |

(List continued on next page.)

FOREIGN PATENT DOCUMENTS

WO95/01842  1/1995  WIPO .

OTHER PUBLICATIONS

PBSC–Collection in patients using the Fresenius–AS 104 Leucollect–protocol, Zingsam et al. believed Crica 1994.
Brown, The Physics of Continuous Flow Centrifugal Cell Separation; Artifical Organs 13(1): 4–20.
Description of a Closed Plastic Bag System for the Collection and Cryopreservation of Leukapheresis–Derived Blood Mononuclear Leukocytes and DFRxc from Human Donors; M. Korbling et al., Infusion, vol. 20, Jun. 1980.

*Primary Examiner*—David A. Reifsnyder
*Attorney, Agent, or Firm*—Daniel D. Ryan; Bradford R. L. Price; Joseph B. Barrett

[57] ABSTRACT

Systems and methods for separating mono nuclear cells from whole blood rotate a separation chamber about a rotational axis. The systems and methods introduce whole blood into a first region of the chamber during its rotation to separate the whole blood into a plasma constituent, red blood cells, and an interface between the red blood cells and the plasma constituent. The interface carries mono nuclear cells. While conveying whole blood into the first region, the systems and methods collect the plasma constituent in the first region, while also collecting the red blood cells in a second region of the chamber spaced from the inlet region. The systems and methods create, while conveying whole blood into the inlet region, a back flow of plasma constituent along the interface from the second region toward the inlet region. This back flow of plasma maintains a high-relative hematocrit in the second region and a low-relative hematocrit in the inlet region. The mono nuclear cells are confined between the low-relative hematocrit inlet region and the high-relative second region. The system and method then convey red blood cells into the second region in a back flow direction toward the inlet region. While conveying red blood cells into the second region, the systems and methods collect the mono nuclear cells in the first region.

13 Claims, 23 Drawing Sheets

U.S. PATENT DOCUMENTS

| Number | Date | Name | Ref |
|---|---|---|---|
| 4,146,172 | 3/1979 | Cullis et al. . | |
| 4,164,318 | 8/1979 | Boggs . | |
| 4,278,202 | 7/1981 | Westberg . | |
| 4,283,004 | 8/1981 | Lamadrid . | |
| 4,386,730 | 6/1983 | Mulzet . | |
| 4,387,848 | 6/1983 | Kellogg et al. . | |
| 4,419,089 | 12/1983 | Kolobow et al. . | |
| 4,425,112 | 1/1984 | Ito . | |
| 4,430,072 | 2/1984 | Kellogg et al. . | |
| 4,447,221 | 5/1984 | Mulzet . | |
| 4,464,167 | 8/1984 | Schoendorfer et al. . | |
| 4,525,155 | 6/1985 | Nillson | 494/37 |
| 4,530,691 | 7/1985 | Brown . | |
| 4,636,193 | 1/1987 | Cullis . | |
| 4,647,279 | 3/1987 | Mulzet et al. . | |
| 4,670,002 | 6/1987 | Koreeda et al. . | |
| 4,675,117 | 6/1987 | Neumann et al. . | |
| 4,708,712 | 11/1987 | Mulzet . | |
| 4,710,161 | 12/1987 | Takabayashi et al. . | |
| 4,724,317 | 2/1988 | Brown et al. . | |
| 4,806,252 | 2/1989 | Brown . | |
| 4,834,890 | 5/1989 | Brown et al. | 210/739 |
| 4,911,833 | 3/1990 | Schoendorfer et al. . | |
| 4,934,995 | 6/1990 | Cullis . | |
| 4,936,820 | 6/1990 | Dennehey et al. . | |
| 5,006,103 | 4/1991 | Bacehowski et al. . | |
| 5,076,911 | 12/1991 | Brown et al. . | |
| 5,078,671 | 1/1992 | Dennehey et al. . | |
| 5,104,526 | 4/1992 | Brown et al. | 210/94 |
| 5,316,667 | 5/1994 | Brown et al. | 210/85 |
| 5,322,620 | 6/1994 | Brown et al. | 210/85 |
| 5,360,542 | 11/1994 | Williamson, IV et al. | 210/380.1 |
| 5,370,802 | 12/1994 | Brown | 210/782 |

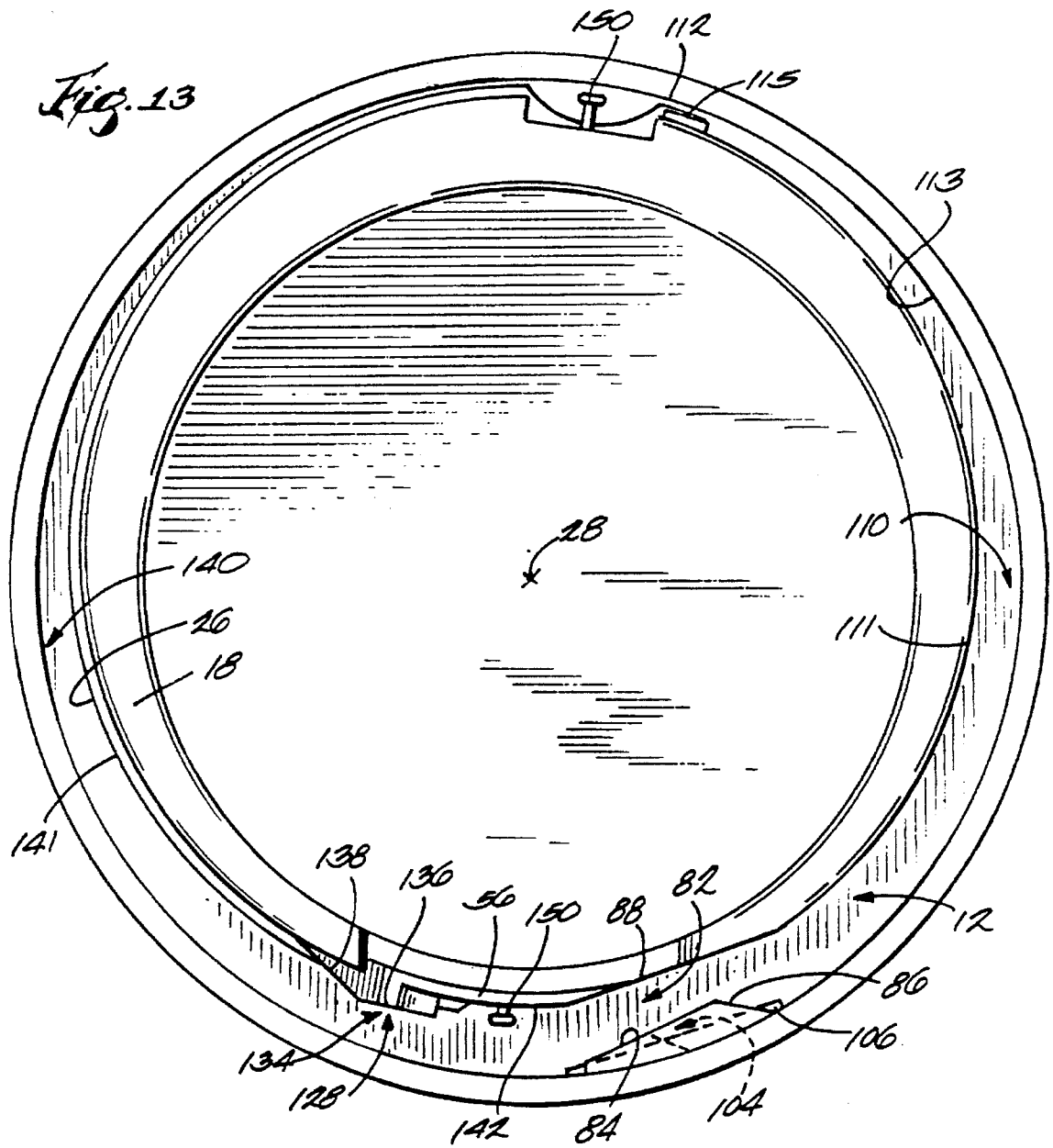

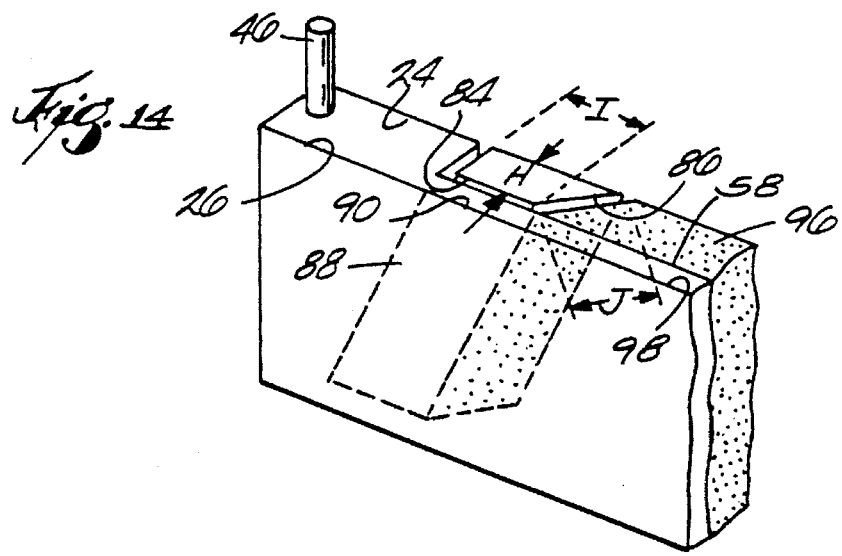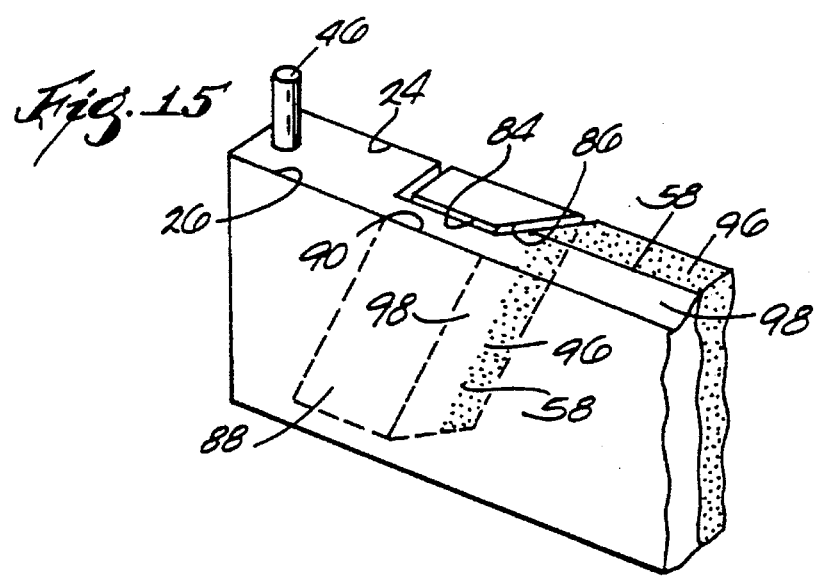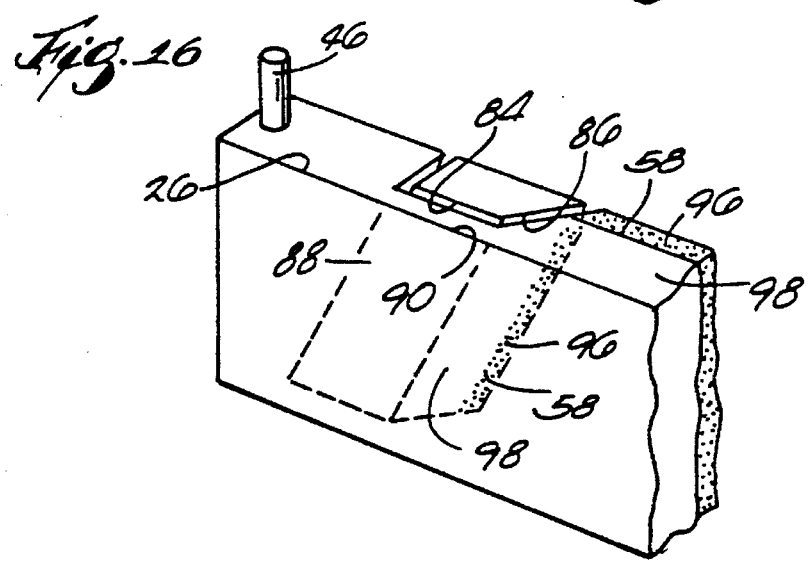

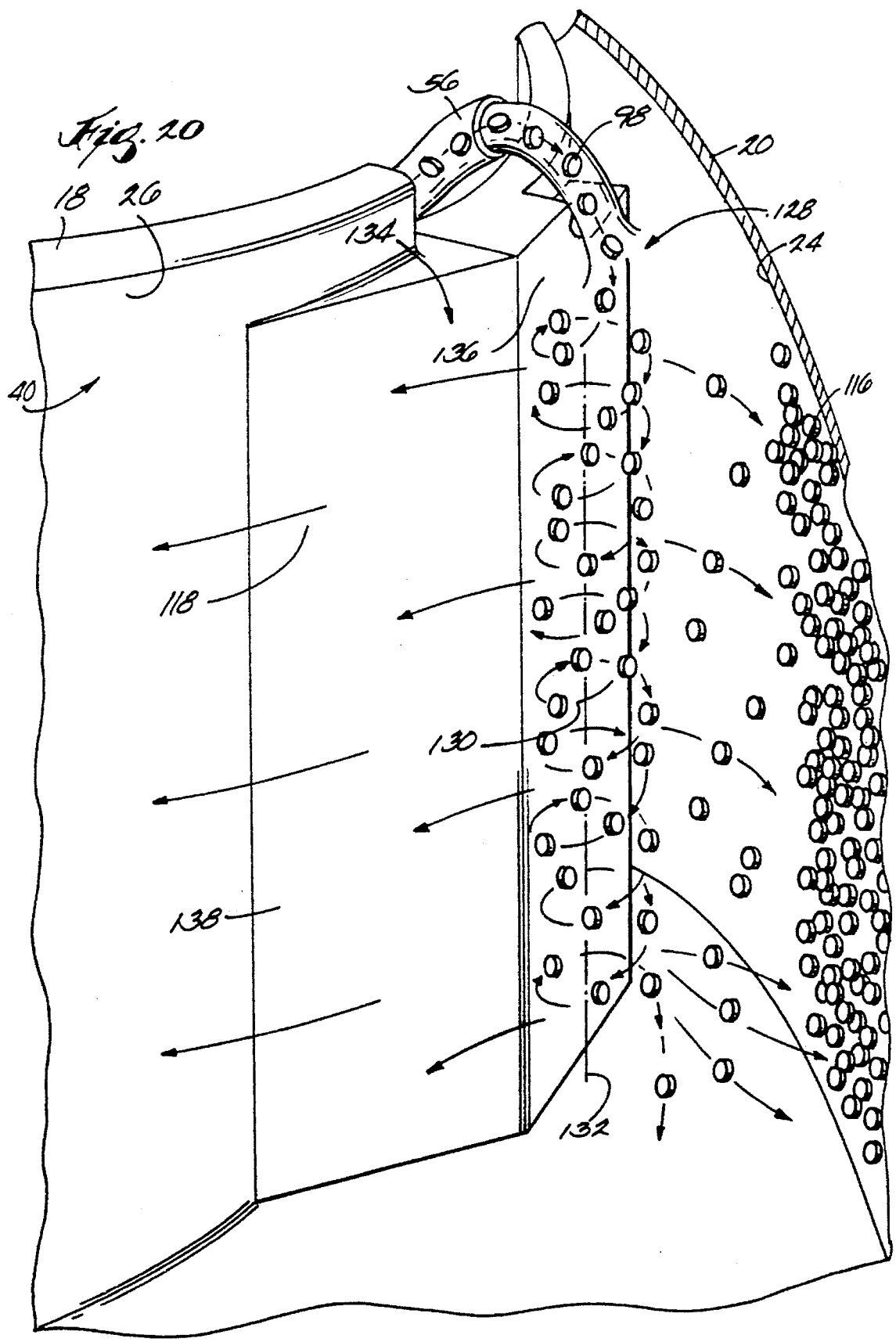

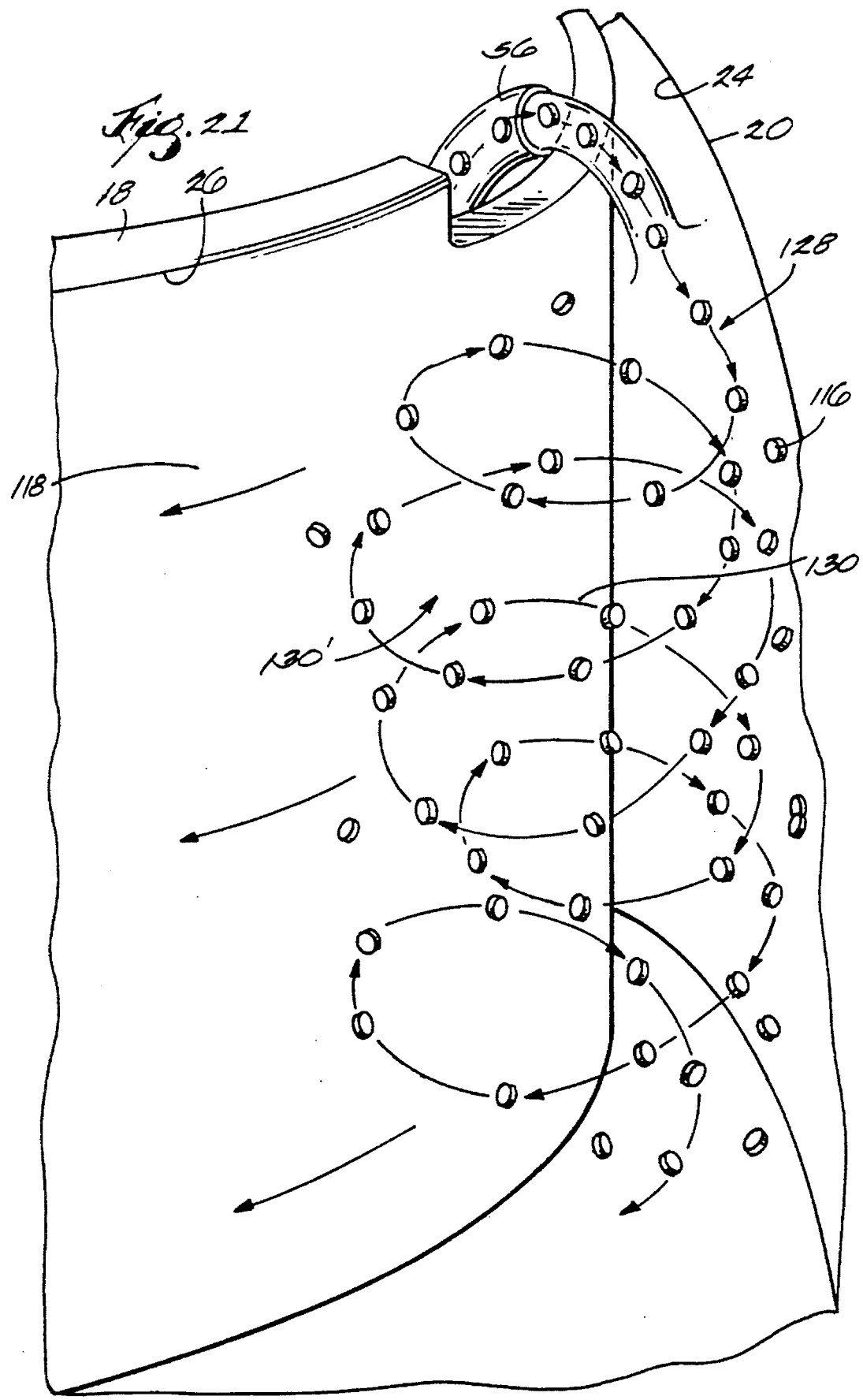

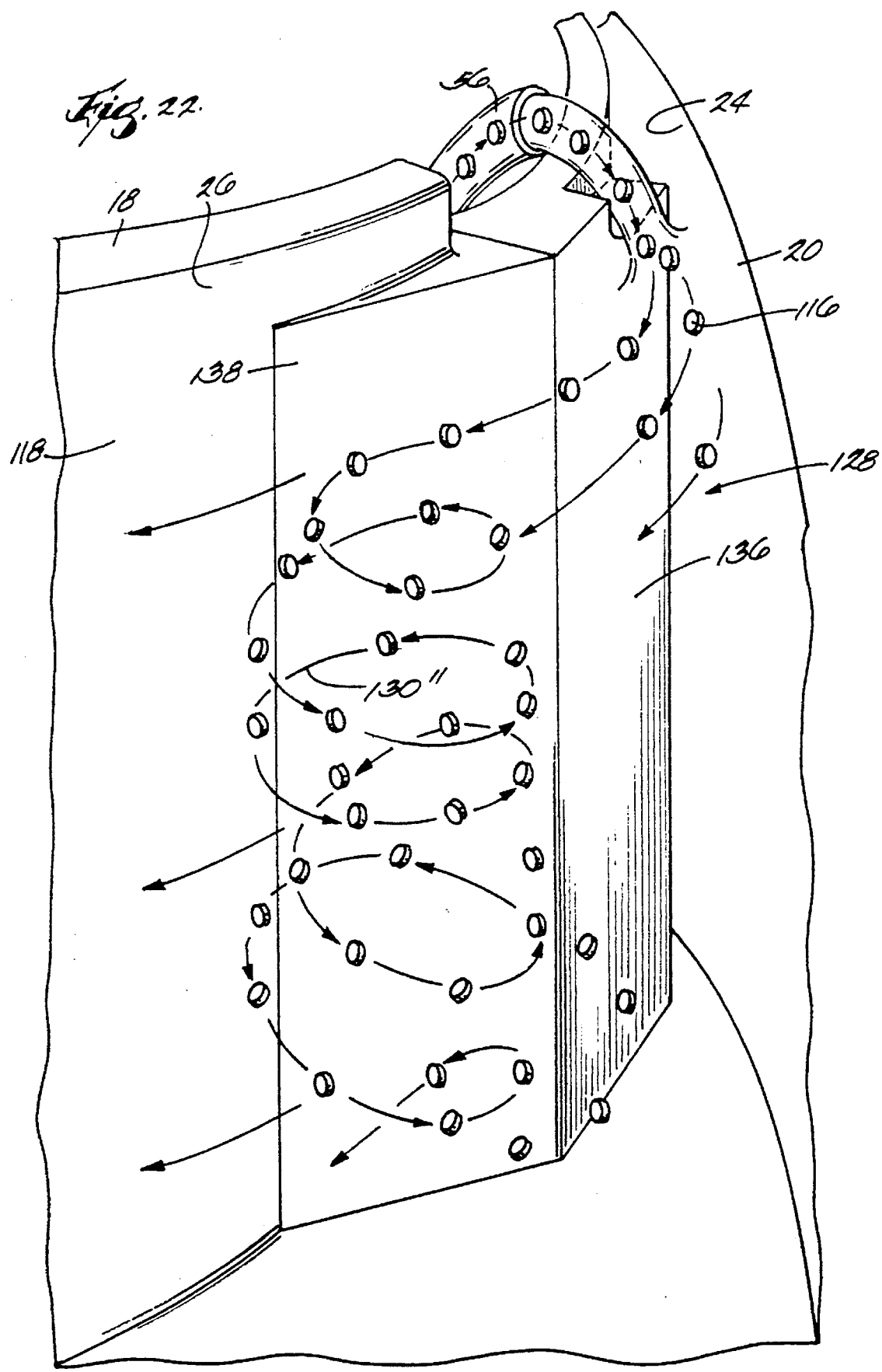

5,573,678

BLOOD PROCESSING SYSTEMS AND METHODS FOR COLLECTING MONO NUCLEAR CELLS

RELATED APPLICATIONS

This application is a continuation-in-part of U.S. patent application Ser. No. 07/814,403 entitled "Centrifuge with Separable Bowl and Spool Elements Providing Access to the Separation Chamber," filed Dec. 23, 1991 (now abandoned). This application is also a continuation-in-part of U.S. patent application Ser. No. 07/748,244 entitled "Centrifugation Pheresis System," filed Aug. 21, 1991 (now U.S. Pat. No. 5,322,620), which is itself a continuation of U.S. patent application Ser. No. 07/514,995, filed May 26, 1989 (now U.S. Pat. No. 5,104,526), which is itself a continuation of U.S. patent application Ser. No. 07/009,179, filed Jan. 30, 1987 (now U.S. Pat. No. 4,834,890).

FIELD OF THE INVENTION

The invention relates to centrifugal processing systems and apparatus.

BACKGROUND OF THE INVENTION

Today blood collection organizations routinely separate whole blood by centrifugation into its various therapeutic components, such as red blood cells, platelets, and plasma.

Conventional blood processing systems and methods use durable centrifuge equipment in association with single use, sterile processing chambers, typically made of plastic. The centrifuge equipment introduces whole blood into these chambers while rotating them to create a centrifugal field.

Whole blood separates within the rotating chamber under the influence of the centrifugal field into higher density red blood cells and platelet-rich plasma. An intermediate layer of leukocytes forms an interface between the red blood cells and platelet-rich plasma. Mono nuclear cells (MNC) are present in the interface.

SUMMARY OF THE INVENTION

The invention provides systems and methods for separating mono nuclear cells from whole blood. The systems and methods rotate a separation chamber about a rotational axis. The systems and methods introduce whole blood into a first region of the chamber during its rotation to separate the whole blood into a plasma constituent, red blood cells, and an interface between the red blood cells and the plasma constituent. The interface carries mono nuclear cells.

While conveying whole blood into the first region, the systems and methods collect the plasma constituent in the first region, while also collecting the red blood cells in a second region of the chamber spaced from the inlet region. The systems and methods confine substantially all the interface in the chamber between the inlet region and the second region.

The system and method then convey red blood cells into the second region in a back flow direction toward the inlet region. While conveying red blood cells into the second region, the systems and methods collect the interface in the first region.

In a preferred embodiment, the systems and methods create, while conveying whole blood into the inlet region, a back flow of plasma constituent along the interface from the second region toward the inlet region. This back flow of plasma maintains a high-relative hematocrit in the second region and a low-relative hematocrit in the inlet region. The mono nuclear cells are confined, or "parked," between the low-relative hematocrit inlet region and the high-relative second region while whole blood is conveyed into the inlet region.

Rotation of the chamber creates a low-G wall radially close to the axis and a high-G wall spaced radially further from the axis than the low-G wall. In a preferred embodiment, while being conveyed into the inlet region, the whole blood is directed through a reduced passage spaced from the high-G wall.

In a preferred embodiment, the interface in the first region lies along a plane. The systems and methods convey the whole blood into the first region through a restricted passage in a plane that is essentially aligned with the plane of the interface.

Other features and advantages of the invention will become apparent upon reviewing the following specification, drawings, and appended claims.

BRIEF DESCRIPTION OF THE DRAWINGS

FIG. 13 is a top view of the spool element positioned within the bowl element, showing the orientation of the high-G and low-G walls along the separation chamber;

FIGS. 14 to 16 somewhat diagrammatically show a portion of the platelet-rich plasma collection zone in the separation chamber, in which the high-G wall surface forms a tapered wedge for containing and controlling the position of the interface between the red blood cells and platelet-rich plasma;

FIG. 20 is a somewhat diagrammatic view of the interior of the processing chamber, looking from the high-G wall toward the low-G wall in the region where platelet-rich plasma begins its separation into platelet concentrate and platelet-poor plasma, showing the formation of optimal vortex flow pattern for perfusing platelet-rich plasma during separation;

FIGS. 21 and 22 are views like FIG. 20, showing the formation of less than optimal vortex flow patterns;

FIG. 27 is a chart showing the location of the MNC collected by the system shown in FIG. 24.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
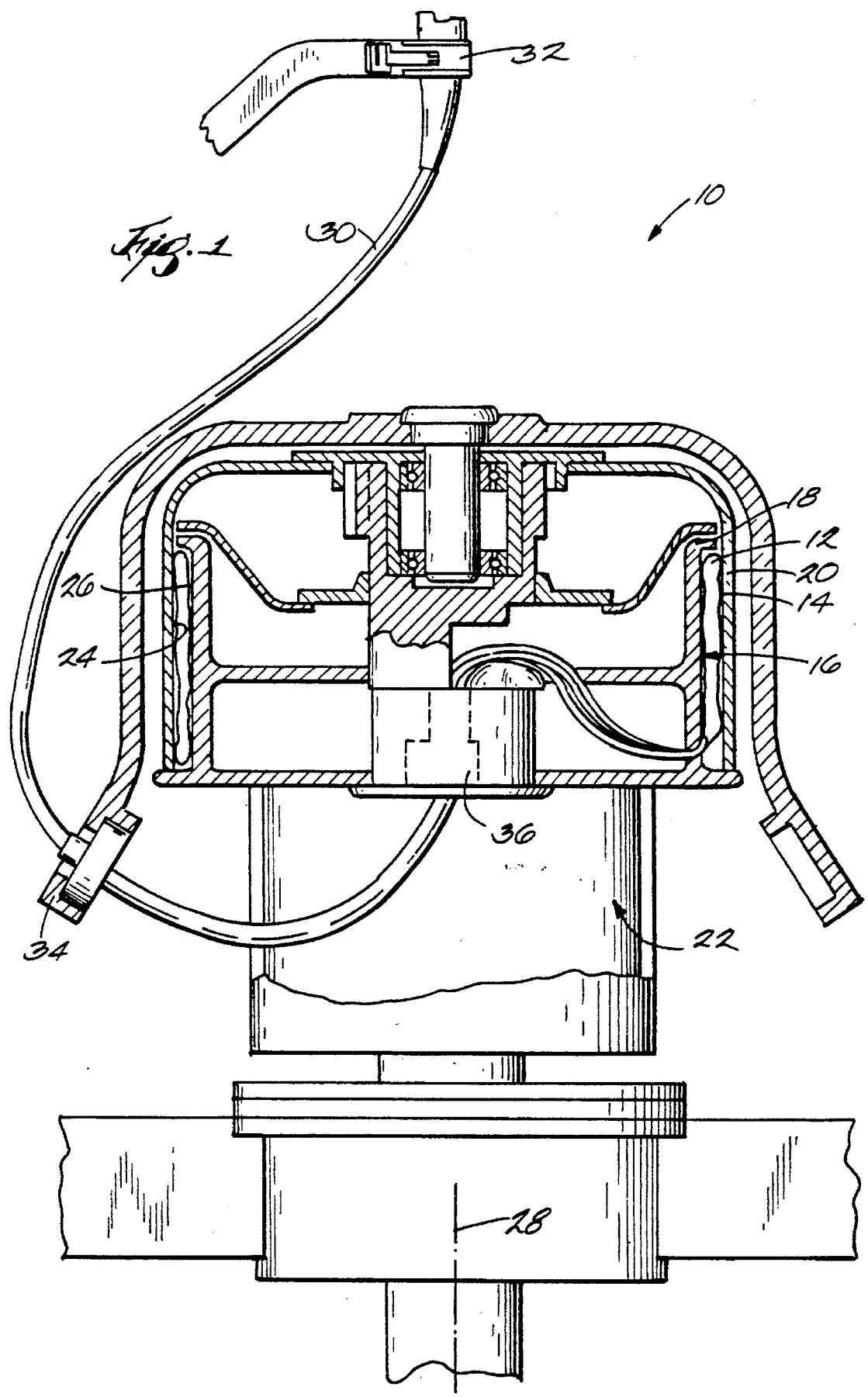
FIG. 1 is a side section view of a blood centrifuge having a separation chamber that embodies features of the invention.
Figure 2:
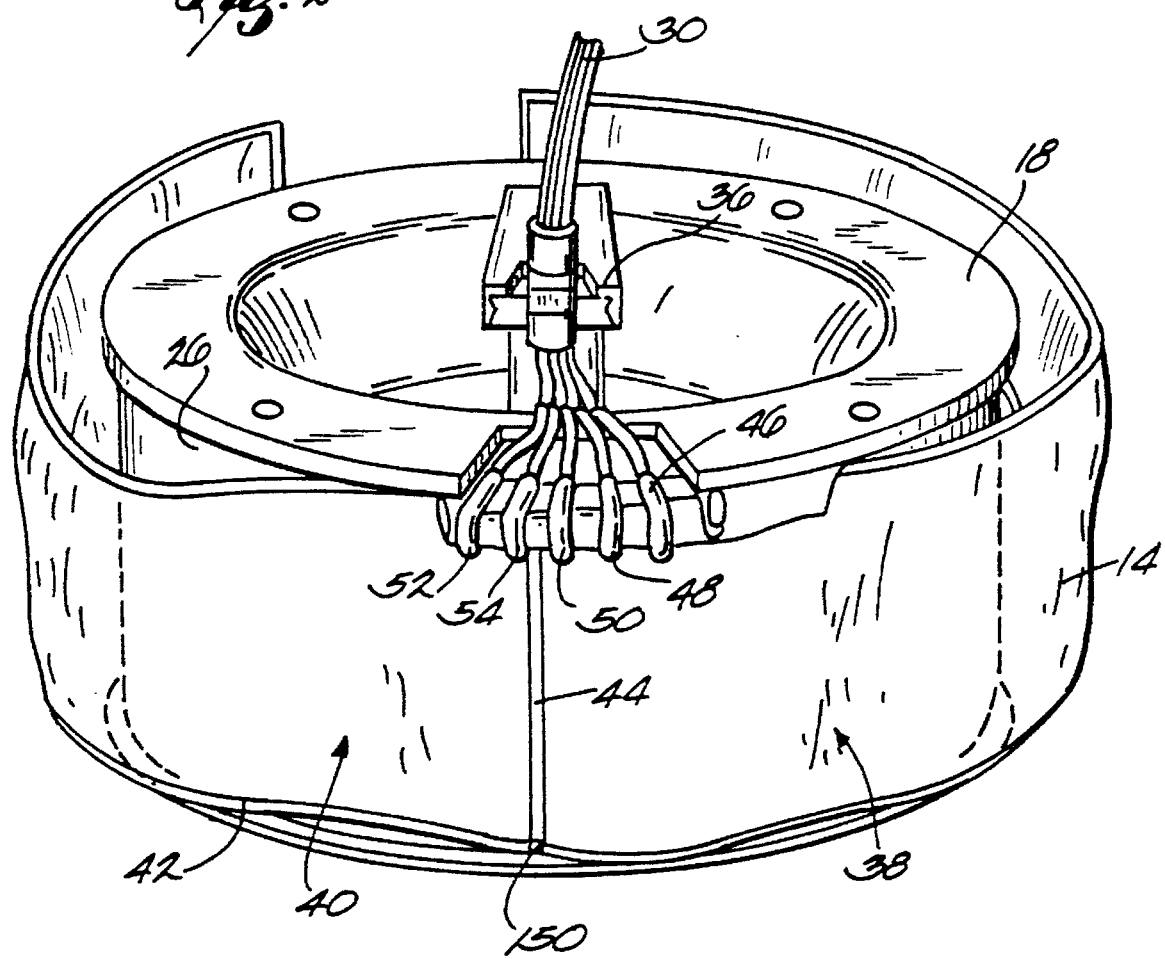
FIG. 2 shows the spool element associated with the centrifuge shown in FIG. 1, with an associated processing container wrapped about it for use.

FIG. 1 shows a blood centrifuge 10 having a blood processing chamber 12 with enhanced platelet separation efficiencies. The boundaries of the chamber 12 are formed by a flexible processing container 14 carried within an annular gap 16 between a rotating spool element 18 and bowl element 20. In the illustrated and preferred embodiment, the processing container 14 takes the form of an elongated tube (see FIG. 3), which is wrapped about the spool element 18 before use, as FIG. 2 shows.

Further details of this centrifuge construction are set forth in U.S. Pat. No. 5,370,802, entitled "Enhanced Yield Platelet Systems and Methods," which is incorporated herein by reference.

Figure 4:
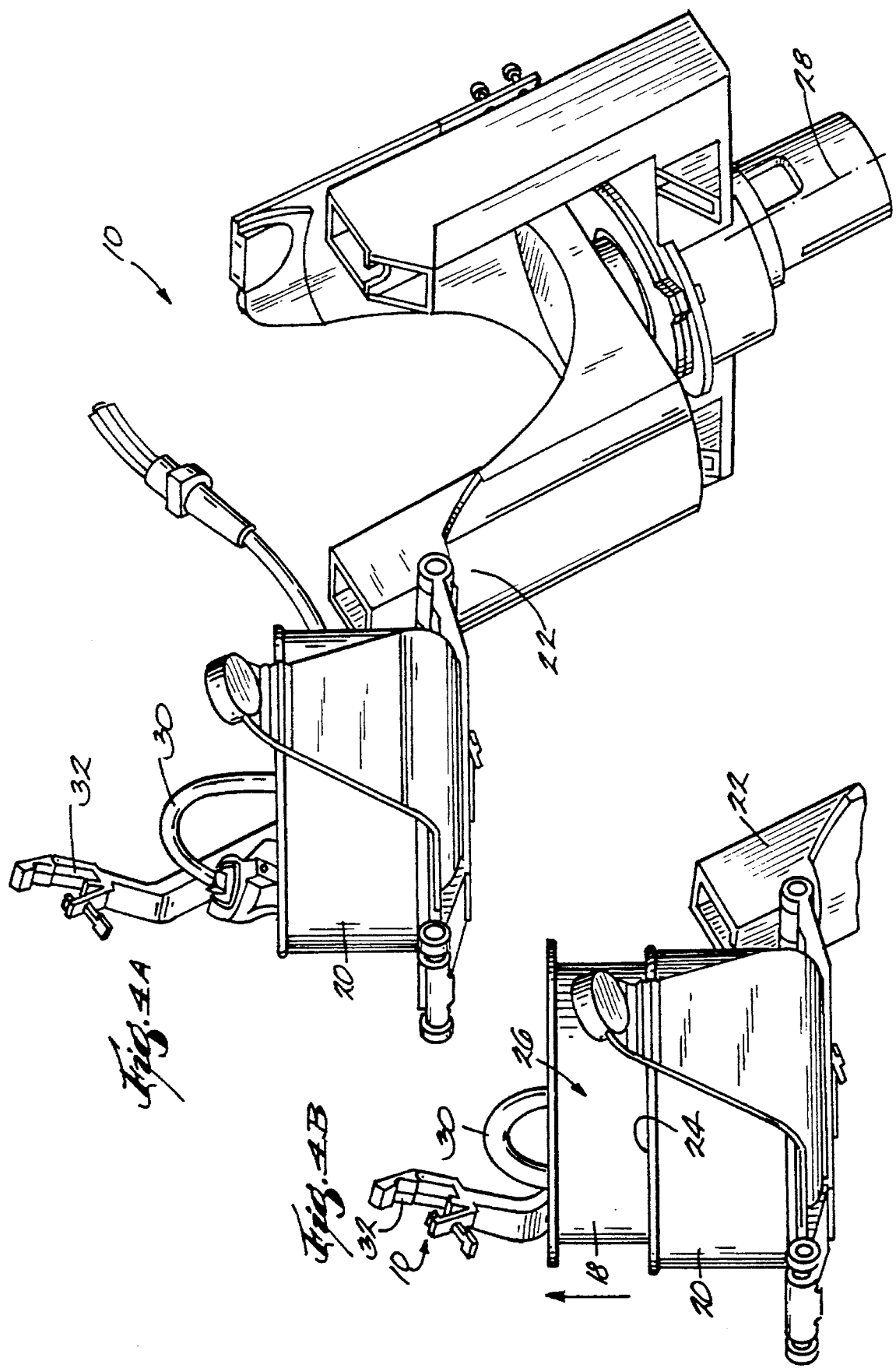
FIG. 4A is a perspective view of the centrifuge shown in FIG. 1, with the bowl and spool elements pivoted into their access position.
FIG. 4B is a perspective view of the bowl and spool elements in their mutually separation condition to allow securing the processing container shown in FIG. 2 about the spool element.
Figure 5:
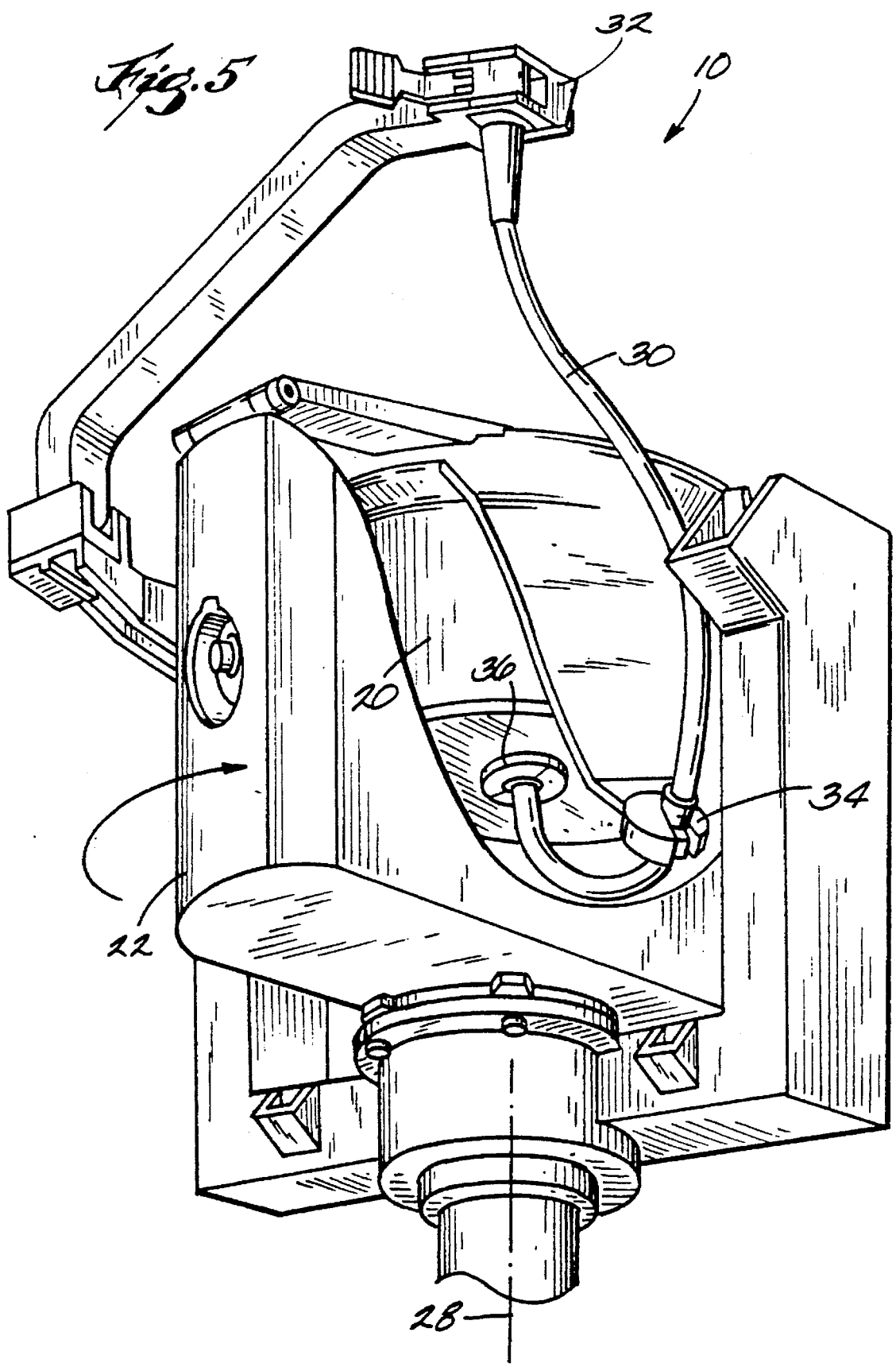
FIG. 5 is a perspective view of centrifuge shown in FIG. 1, with the bowl and spool elements pivoted into their operational position.

The bowl and spool elements 18 and 20 are pivoted on a yoke 22 between an upright position, as FIGS. 4A/4B show, and a suspended position, as FIGS. 1 and 5 show.

When upright (see FIG. 4A), the bowl and spool elements 18 and 20 are presented for access by the user. A mechanism permits the spool and bowl elements 18 and 20 to assume a mutually separated position, as FIG. 4B shows. In this position, the spool element 18 is at least partially out of the interior area of the bowl element 20 to expose the exterior spool surface for access. When exposed, the user can wrap the container 14 about the spool element 20 (as FIG. 2 shows). Pins 150 on the spool element 20 (see, e.g., FIGS. 6; 10; and 11) engage cutouts on the container 14 to secure the container 14 on the spool element 20.

The mechanism (not shown) also permits the spool and bowl elements 18 and 20 to assume a mutually cooperating position, as FIG. 4A shows. In this position, the spool element 20 and the secured container 14 are enclosed within the interior area of the bowl element 18.

Further details of the mechanism for causing relative movement of the spool and bowl elements 18 and 20 as just described are disclosed in U.S. Pat. No. 5,360,542 entitled "Centrifuge With Separable Bowl and Spool Elements Providing Access to the Separation Chamber," which is incorporated herein by reference.

When closed, the spool and bowl elements 18 and 20 can be pivoted into a suspended position, as FIGS. 1 and 5 show. When suspended, the bowl and spool elements 18 and 20 are in position for operation.

In operation, the centrifuge 10 rotates the suspended bowl and spool elements 18 and 20 about an axis 28, creating a centrifugal field within the processing chamber 12.

The radial boundaries of the centrifugal field (see FIG. 1) are formed by the interior wall 24 of the bowl element 18 and the exterior wall 26 of the spool element 20. The interior bowl wall 24 defines the high-G wall. The exterior spool wall 26 defines the low-G wall.

An umbilicus 30 (see FIG. 1) communicates with the interior of the processing container 14 within the centrifugal field and with pumps and other stationary components located outside the centrifugal field. A non-rotating (zero omega) holder 32 holds the upper portion of the umbilicus 30 in a non-rotating position above the suspended spool and bowl elements 18 and 20. A holder 34 on the yoke 22 rotates the mid-portion of the umbilicus 30 at a first (one omega) speed about the suspended spool and bowl elements 18 and 20. Another holder 36 rotates the lower end of the umbilicus 30 at a second speed twice the one omega speed (the two omega speed), at which the suspended spool and bowl elements 18 and 20 also rotate. This known relative rotation of the umbilicus 30 keeps it untwisted, in this way avoiding the need for rotating seals.

As the spool and bowl elements 18 and 20 rotate about the axis 28, blood is introduced into the container 14 through the umbilicus 30. The blood follows a circumferential flow path within the container 14 about the rotational axis 28. When conveying blood, the sidewalls of the container 14 expand to conform to the profiles of the exterior (low-G) wall 26 of the spool element 18 and the interior (high-G) wall 24 of the bowl element 20.

In the illustrated and preferred embodiment (see FIGS. 2 and 3), the processing container 14 is divided into two functionally distinct processing compartments 38 and 40. More particularly (see FIGS. 2 and 3), a first peripheral seal 42 forms the outer edge of the container. A second interior seal 44 extends generally parallel to the rotational axis 28, dividing the container 14 into the first processing compartment 38 and the second processing compartment 40.

Three ports 46/48/50 attached to tubing extending from the umbilicus 30 communicate with the first compartment 38. Two additional ports 52 and 54 attached to tubing extending from the umbilicus 30 communicate with the second compartment 40.

Figure 6:
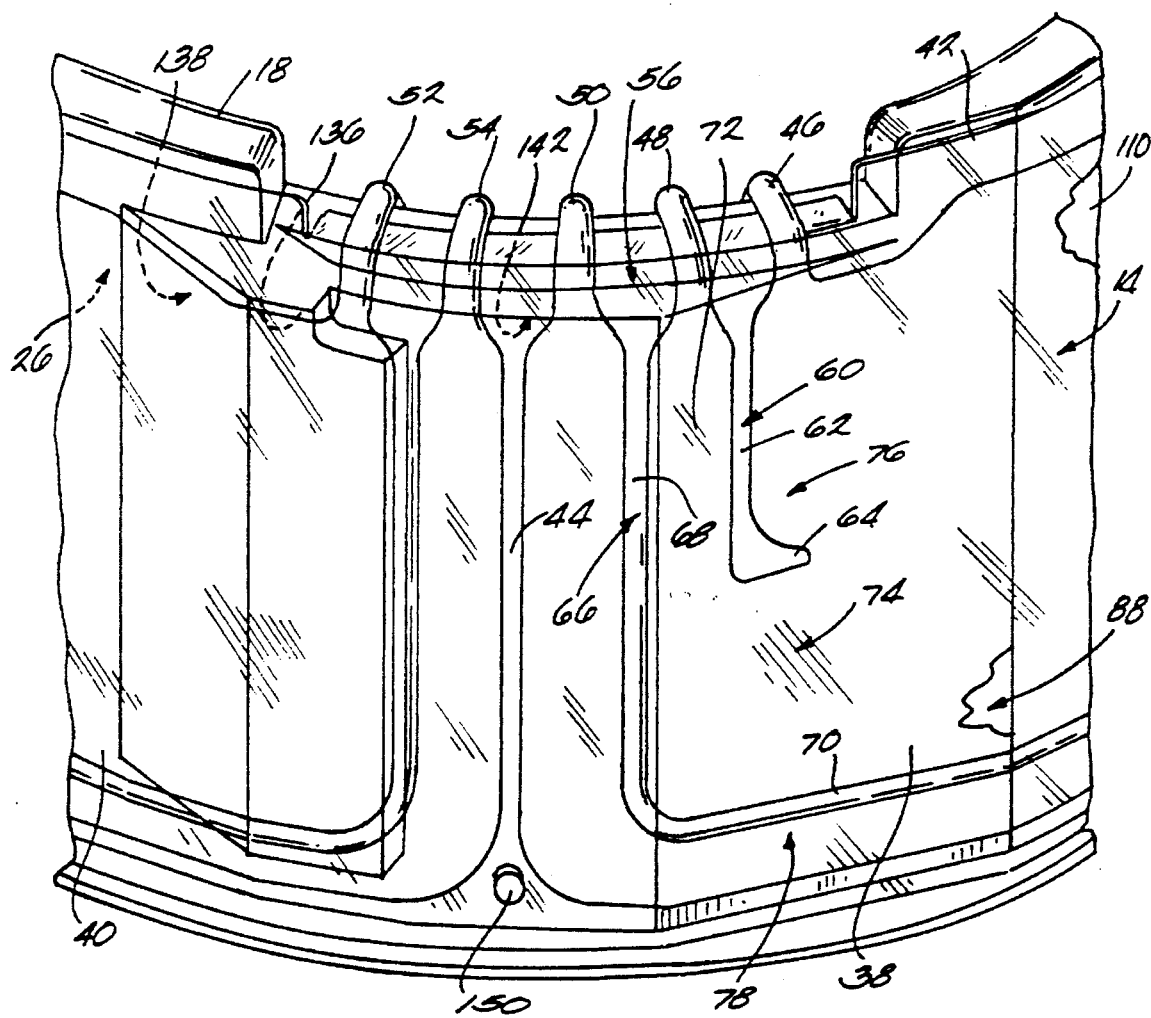
FIG. 6 is an enlarged perspective view of a portion of the processing container shown in FIG. 3 secured to the spool element of the centrifuge, also showing the orientation of the ports serving the interior of the processing chamber and certain surface contours of the spool element.
Figure 10:
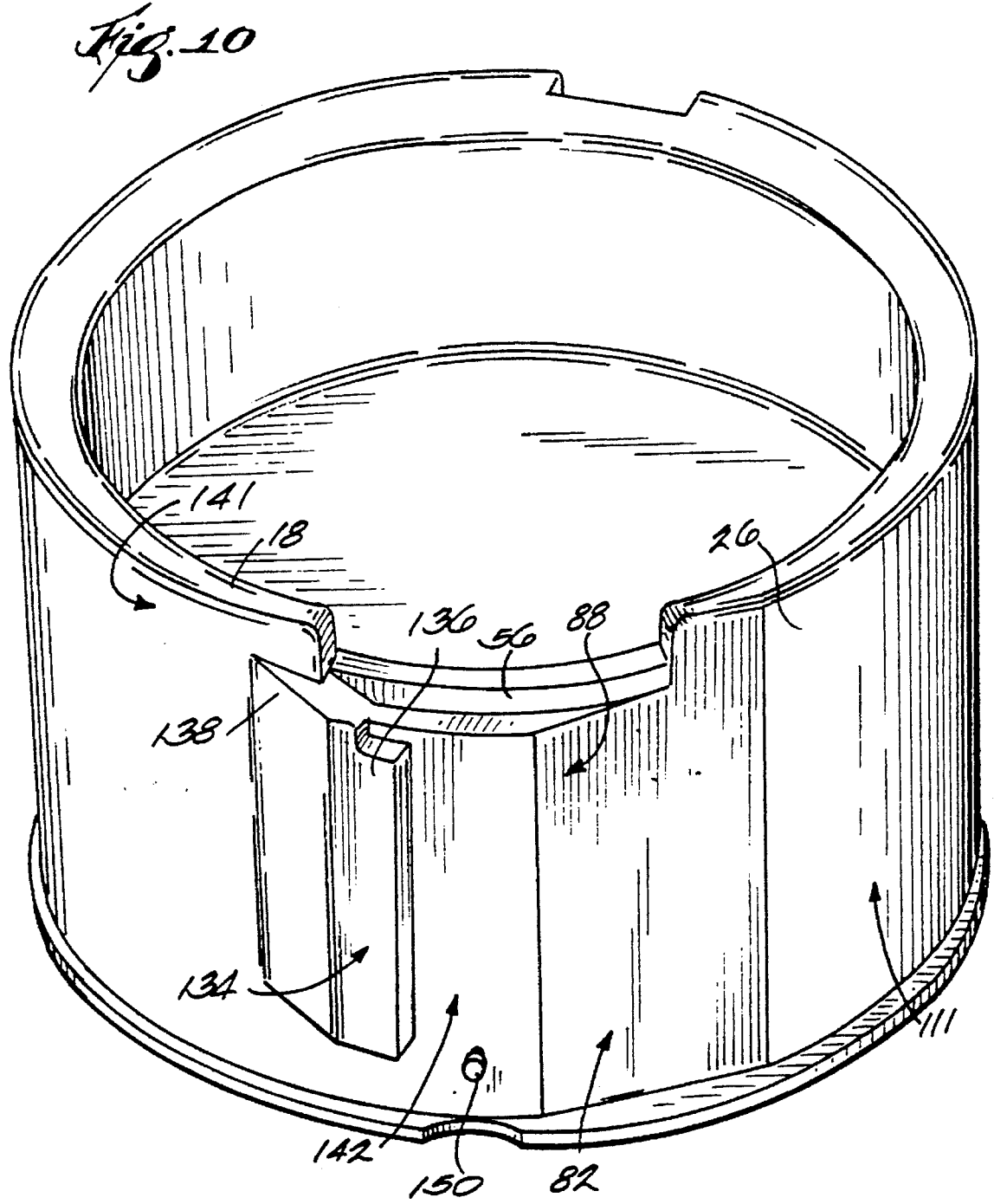
FIGS. 10 to 12 are perspective exterior views of the spool element, showing the sequential non-iso-radial regions about the circumference of the low-G wall.

As FIG. 6 best shows, the five ports 46 to 54 are arranged side-by-side along the top transverse edge of the container 14. When the container 14 is secured to the spool element 18, the ports 46 to 54 are all oriented parallel to the axis of rotation 28. The upper region of the exterior wall 26 spool element 18 includes a lip region 56 against which the ports 46 to 54 rest when the container 14 is secured to the spool element 18 for use. FIG. 10 also shows the lip region 56. The lip region 56 extends along an arc of equal radius from the axis of rotation 28. Thus, all ports 46 to 54 open into the compartments 38 and 40 at the same radial distance from the rotational axis 28.

Each processing compartment 38 and 40 serves a separate and distinct separation function, as will now be described in greater detail.

Separation in the First Processing Compartment

The first compartment 38 receives whole blood (WB) through the port 48. As FIG. 7 best shows, the whole blood separates in the centrifugal field within the first compartment 38 into red blood cells (RBC, designated by numeral 96), which move toward the high-G wall 24, and platelet-rich plasma (PRP, designated by numeral 98), which are displaced by movement of the RBC 96 toward the low-G wall 26. The port 50 (see FIGS. 3 and 6) conveys RBC 96 from the first compartment 38, while the port 46 conveys PRP 98 from the first compartment 38.

In the first processing compartment 38, an intermediate layer, called the interface (designed by numeral 58)(see FIG. 7), forms between the RBC 96 and PRP 98. Absent efficient separation conditions, platelets can leave the PRP 98 and settle on the interface 58, thereby lessening the number of platelets in PRP 98 conveyed by the port 46 from the first compartment 38.

The first compartment 38 (see FIGS. 3 and 7) includes a third interior seal 60 located between the PRP collection port 48 and the WB inlet port 50. The third seal 60 includes a first region 62, which is generally parallel to the rotational axis 28. The third seal also includes a dog-leg portion 64, which bends away from the WB inlet port 48 in the direction of circumferential WB flow in the first compartment 38. The dog-leg portion 64 terminates beneath the inlet of the PRP collection port 48.

The first compartment 38 (see FIG. 3) also includes a fourth interior seal 66 located between the WB inlet port 48 and the RBC collection port 50. Similar to the third seal 60, the fourth seal 66 includes a first region 68, which is generally parallel to the rotational axis 28, and a dog-leg portion 70, which bends away from the RBC collection port 52 in the direction of circumferential WB flow in the first compartment 38. The dog-leg portion 70 of the fourth seal 66 extends beneath and beyond the dog-leg portion 64 of the third seal 60. The dog-leg portion 70 terminates near the longitudinal side edge of the first compartment 38 opposite to the longitudinal side edge formed by the second interior seal 44.

Figure 7:
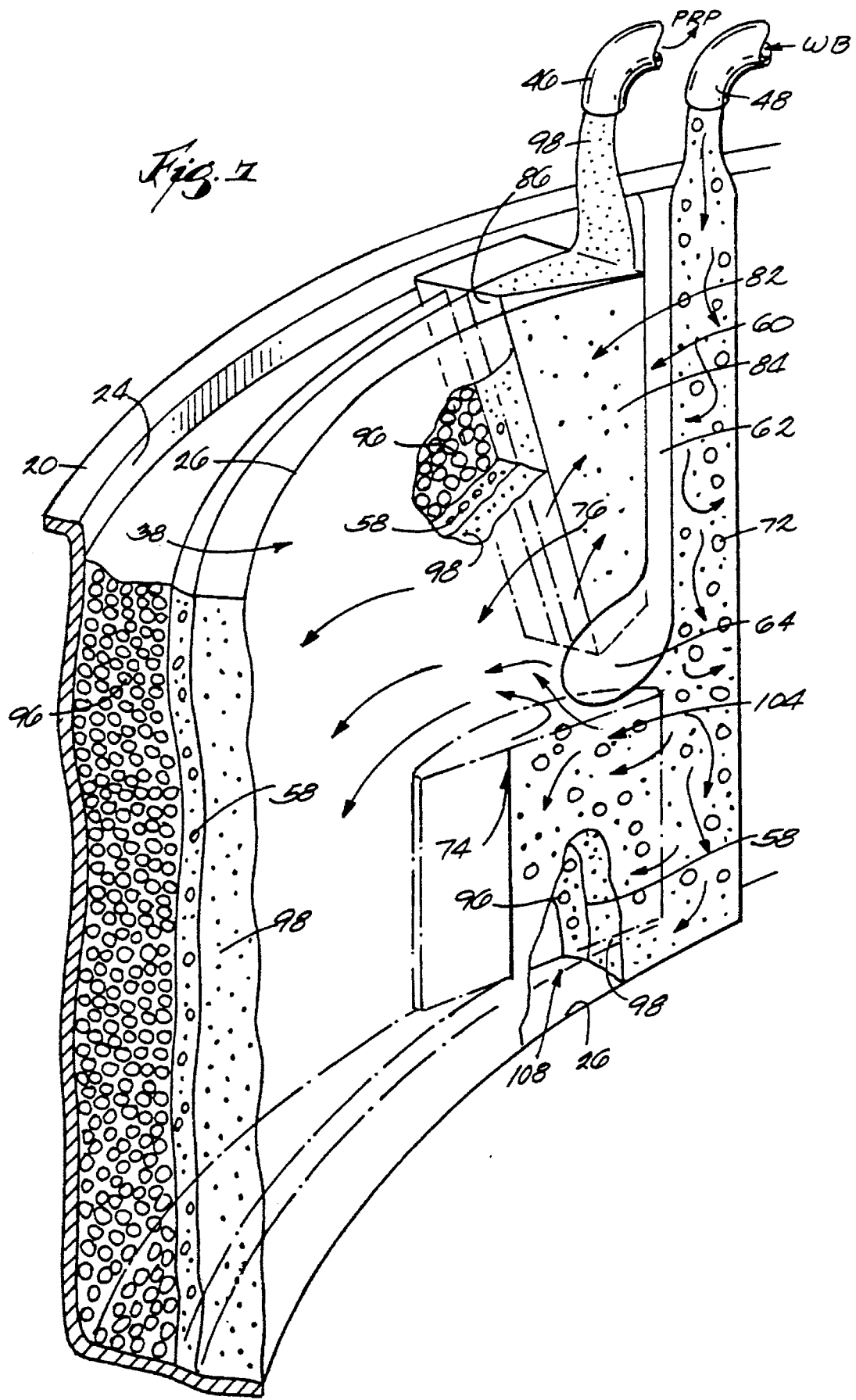
FIG. 7 is a somewhat diagrammatic view of the interior of the processing chamber, looking from the low-G wall toward the high-G wall in the region where whole blood enters the processing chamber for separation into red blood cells and platelet-rich plasma, and where platelet-rich plasma is collected in the processing chamber.

Together, the third and fourth interior seals 60 and 66 form a WB inlet passage 72 that first extends along the axis of rotation and then bends to open in the direction of intended circumferential flow within the first compartment 38, there defining a WB entry region 74, of which FIG. 7 shows an interior view). The third interior seal 60 also forms a PRP collection region 76 within the first compartment 38, of which FIG. 7 also shows an interior view.

As FIG. 7 best shows, the WB entry region 74 is next to the PRP collection region 76. This close juxtaposition creates dynamic flow conditions that sweep platelets into the PRP collection region 76.

More particularly, the velocity at which the RBC 96 settle toward the high-G wall 24 in response to centrifugal force is greatest in the WB entry region 74 than elsewhere in the first compartment 38. Further details of the distribution of RBC 96 during centrifugation in a chamber are set forth in Brown, "The Physics of Continuous Flow Centrifugal Cell Separation," *Artificial Organs*, 13(1):4–20 (1989).

There is also relatively more plasma volume to displace toward the low-G wall 26 in the WB entry region 74. As a result, relatively large radial plasma velocities toward the low-G wall 26 occur in the WB entry region 74. These large radial velocities toward the low-G wall 26 elute large numbers of platelets from the RBC 96 into the close-by PRP collection region 76.

Figure 3:
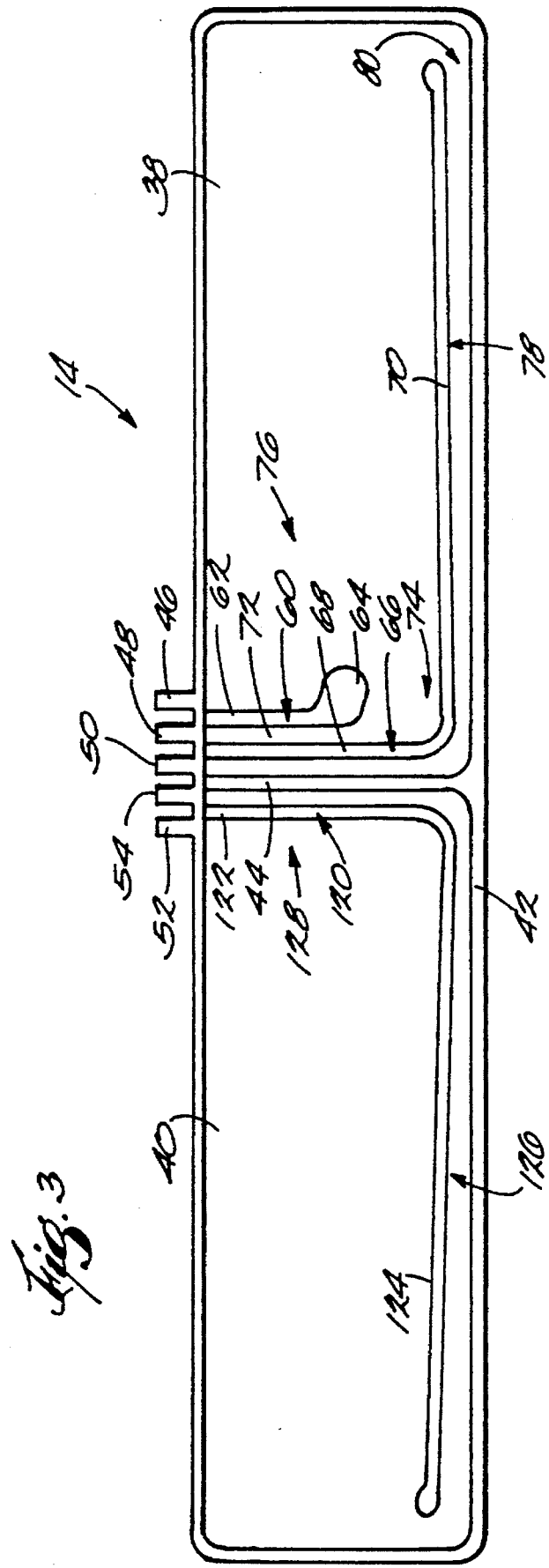
FIG. 3 is a top view of the processing chamber shown in FIG. 2.

Together, the fourth interior seal 66, the second interior seal 44, and the lower regions of the first peripheral seal 42 form a RBC collection passage 78 (see FIG. 3). The RBC collection passage 78 extends first along the axis of rotation 28 and then bends in a circumferential path to open near the end of the intended WB circumferential flow path, which comprises a RBC collection region 80.

Figure 8:
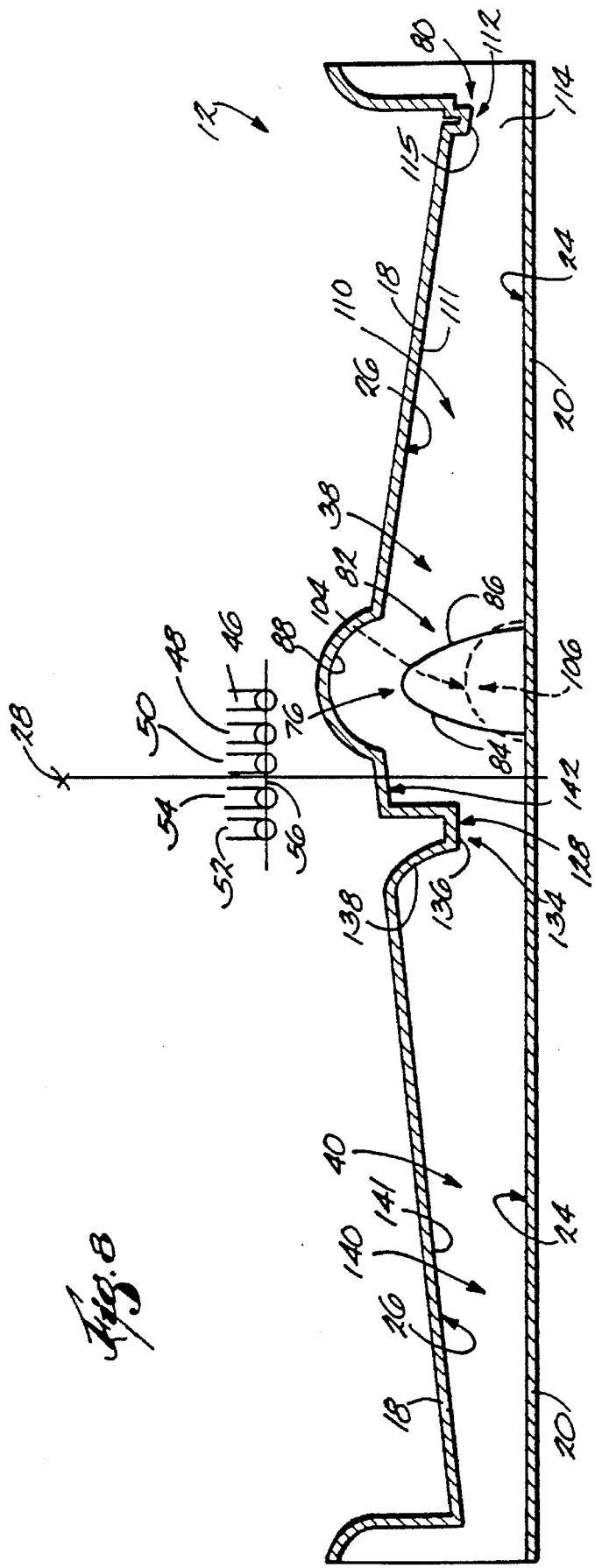
FIG. 8 is a diagrammatic top view of the separation chamber of the centrifuge shown in FIG. 1, laid out to show the radial contours of the high-G G and low-G walls.

As FIG. 8 shows, the contoured surface of the exterior wall 26 of the spool element 18 bounding the low-G side of the first compartment 38 continuously changes in terms of its radial distance from the rotational axis 28. At no time does the exterior (low-G) wall 26 of the spool element 18 comprise an iso-radial contour with respect to the rotational axis 28. On the other hand, the surface of the interior (high-G) wall 24 of the bowl element 20 bounding the high-G side of the first compartment is iso-radial with respect to the rotational axis 28, except for two localized, axially aligned regions in the first compartment 38, where the radial contours change. The juxtaposition of these contoured surfaces on the exterior (low-G) wall 26 of the spool element 18 and the interior (high-G) wall of the bowl element 20 bounding the first compartment 38 further enhance the separation conditions that the interior structure of the compartment 38 create.

Figure 9:
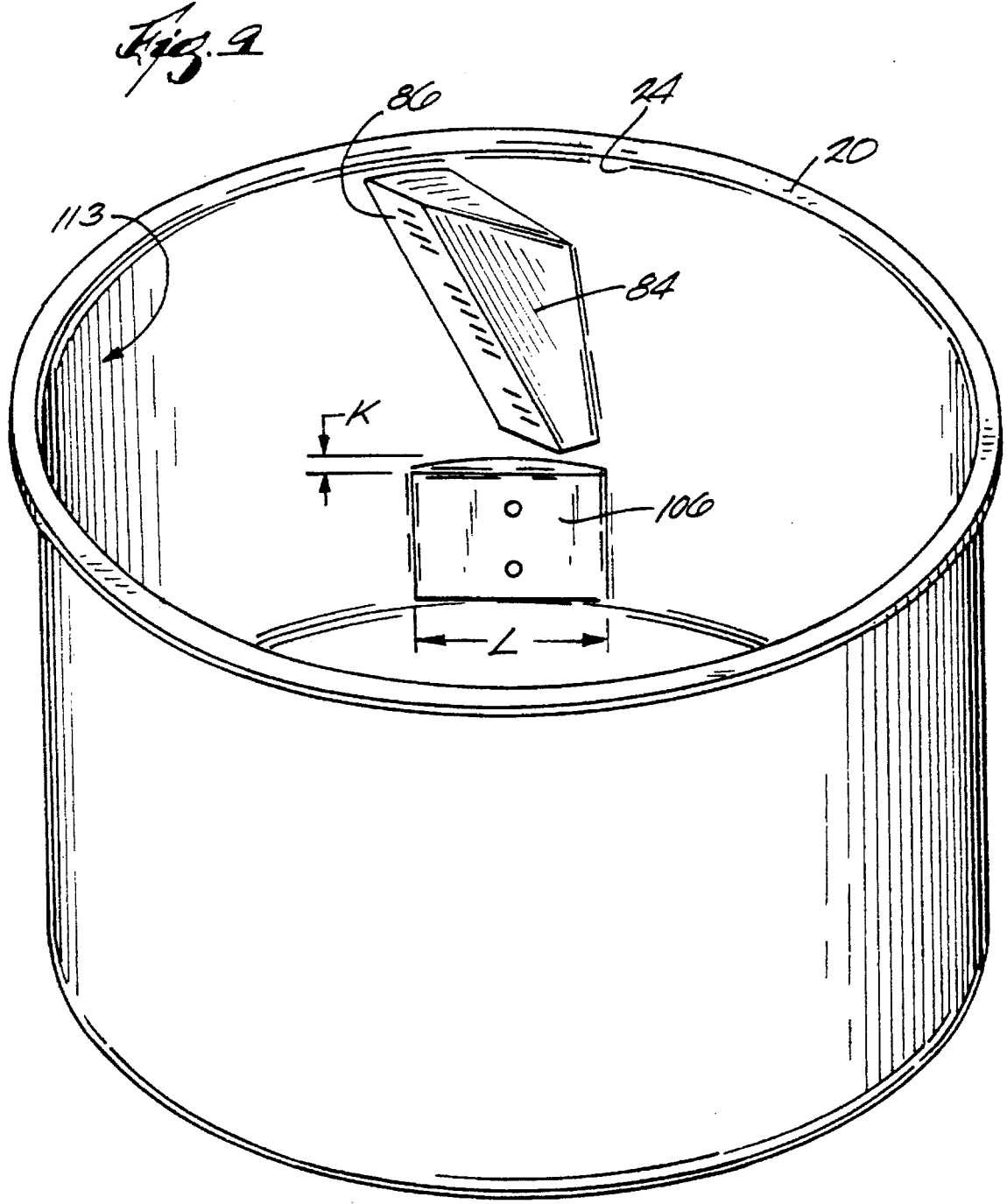
FIG. 9 is a perspective interior view of the bowl element, showing the two regions where the high-G wall is not iso-radial.

More particularly, the juxtaposed surface contours of the high-G and low-G walls 24 and 26 create a first dynamic flow zone 82 in the PRP collection region 76 of the first compartment 38. There, the contour of the high-G wall 24 forms a tapered wedge (see FIG. 9) comprising first and second tapered surfaces 84 and 86. These surfaces 24 project from the high-G wall 24 toward the low-G wall 26. The slope of the first tapered surface 84 is less than the slope of the second tapered surface 86; that is, the second tapered surface 86 is steeper in pitch than the first tapered surface 84.

Radially across from the tapered surfaces 84 and 86, the contour of the low-G exterior wall 26 of the spool element 18 forms a flat surface 88 (see FIGS. 10 and 13). In terms of its radial dimensions (which FIG. 8 shows), the flat surface 88 first decreases and then increases in radius in the direction of WB flow in the first compartment 38. The flat surface 88 thereby presents a decrease and then an increase in the centrifugal field along the low-G wall 26. The flat surface 88 provides clearance for the first and second tapered surfaces 84 and 86 to accommodate movement of the spool and bowl elements 18 and 20 between their mutually separated and mutually cooperating positions. The flat surface 88 also creates a second dynamic flow zone 104 in cooperation with a flat surface 106 facing it on the high-G wall 24 in the WB entry region 74 (see FIG. 9), as will be described in greater detail later.

As FIGS. 14 to 16 show, the facing first surface 84 and flat surface 88 in the first zone 82 form a constricted passage 90 along the low-G wall 26, along which the PRP 98 layer extends. As shown diagrammatically in FIGS. 14 to 16, the tapered surface 86 diverts the fluid flow along the high-G wall 24 of the first compartment 38, keeping the interface 58 and RBC 96 away from the PRP collection port 46, while allowing PRP 98 to reach the PRP collection port 46.

This flow diversion also changes the orientation of the interface 58 within the PRP collection region 76. The second tapered surface 86 displays the interface 26 for viewing through a side wall of the container by an associated interface controller (not shown). Further details of a preferred embodiment for the interface controller 134 are described in U.S. Pat. No. 5,316,667, which is incorporated herein by reference.

The interface controller monitors the location of the interface 58 on the tapered surface 86. As FIGS. 14 to 16 show, the position of the interface 58 upon the tapered surface 86 can be altered by controlling the relative flow rates of WB, the RBC 96, and the PRP through their respective ports 48, 50, and 46. The controller 134 varies the rate at which PRP 98 is drawn from the first compartment 38 to keep the interface 58 at a prescribed preferred location on the tapered surface 86 (which FIG. 15 shows), away from the constricted passage 90 that leads to the PRP collection port 46. Alternatively, or in combination, the controller 134 could control the location of the interface 58 by varying the rate at which WB is introduced into the first compartment 38, or the rate at which RBC are conveyed from the first compartment 134, or both.

Figure 17:
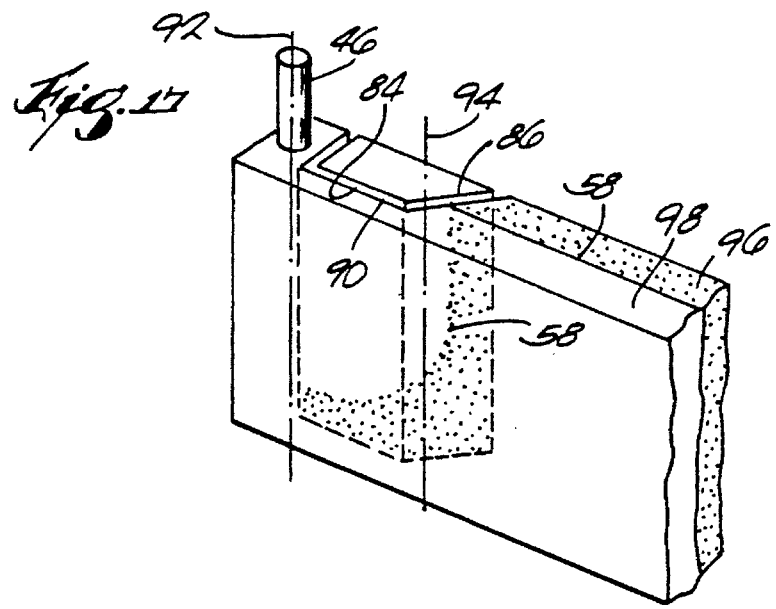
FIGS. 17 to 19 show the importance of slanting the tapered wedge with respect to the axis of the platelet-rich plasma collection port.

In the illustrated and preferred embodiment (see FIGS. 17 to 19), the major axis 94 of the tapered surface 86 is oriented at a non-parallel angle α with respect to the axis 92 of the PRP port 46. The angle α is greater than 0° (i.e., when the surface axis 94 is parallel to the port axis 92, as FIG. 17 shows), but is preferably less than about 45°, as FIG. 19 shows. Most preferably, the angle α is about 30°.

When the angle α is at or near 0° (see FIG. 17), the boundary of the interface 58 between RBC 96 and PRP 98 is not uniform along the tapered surface 86. Instead, the boundary of the interface 58 bulges toward the tapered surface 84 along the region of the surface 86 distant to the port 46. RBC 96 spill into the constricted passage 90 and into the PRP 98 exiting the PRP port 46.

When the angle α is at or near 45° (see FIG. 19), the boundary of the interface 58 between RBC 96 and PRP 98 is also not uniform along the tapered surface 86. Instead, the boundary of the interface 58 bulges toward the tapered surface 84 along the region of the surface 86 close to the port 46. RBC 96 again spill into constricted passage 90 and into the PRP 98 exiting the PRP port 46.

Figure 18:
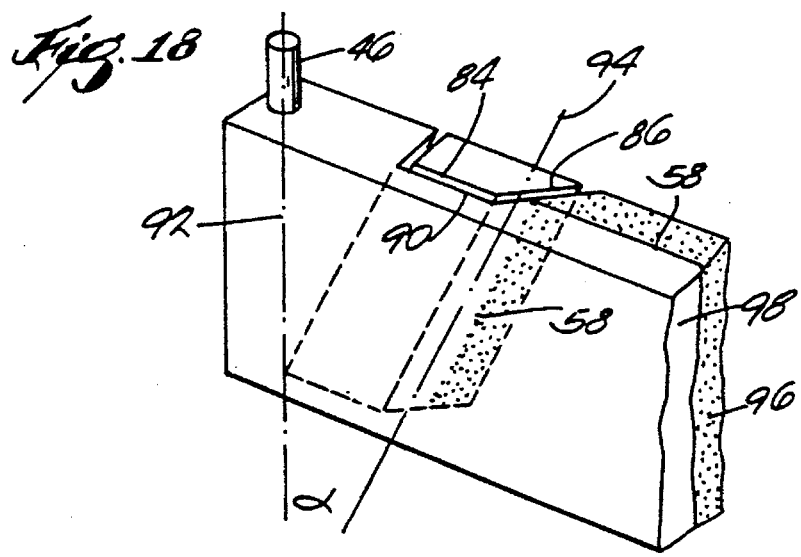
Figure 19:
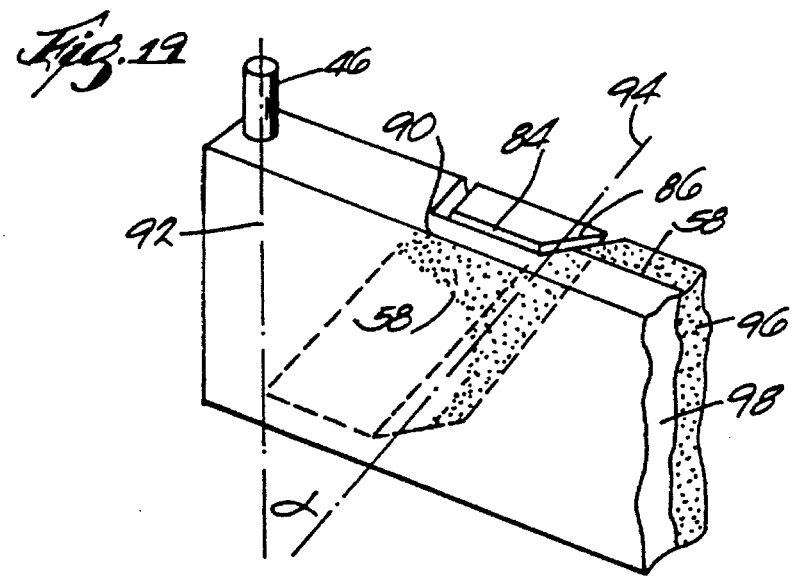

As FIG. 18 shows, by presenting the desired angle α, the collected PRP 98 is kept essentially free of RBC 96 and leukocytes.

The juxtaposed surface contours of the high-G and low-G walls 24 and 26 further create a second dynamic flow zone 104 in the WB entry region 74 of the first compartment 38. There, the contour of the high-G wall 24 forms a flat surface 106 (see FIG. 9) spaced along the rotational axis 28 below the tapered surfaces 84 and 86. The flat surface 106 also faces the already described flat surface 88 on the low-G wall 26 (see FIG. 13). In terms of its radial dimensions (which FIG. 8 shows), the flat surface 106 on the high-G wall 24 first decreases and then increases in radius in the direction of WB flow in the first compartment 38. The flat surface 106 thereby presents a decrease and then an increase in the centrifugal field along the high-G wall 24.

The boundaries of the first and second zones 82 and 104 are generally aligned in an axial direction with each other on the high-G wall 24 (see FIG. 7), as well as radially aligned with the boundaries of the flat surface 88 on the low-G wall 26 (see FIG. 13). The first and second zones 82 and 104 therefore circumferentially overlap in a spaced relationship along the axis of rotation 28 in the first compartment 38.

This juxtaposition of the two zones 82 and 104 enhances the dynamic flow conditions in both the WB entry region 74 and PRP collection region 76. The radially opposite flat surfaces 88 and 106 of the second zone 104 form a flow-restricting dam on the high-G wall 24 of the WB entry region 74. Flow of WB in the WB inlet passage 72 is generally confused and not uniform (as FIG. 7 shows). The zone dam 104 in the WB entry region 74 restricts WB flow to a reduced passage 108, thereby causing more uniform perfusion of WB into the first compartment 38 along the low-G wall 26.

The juxtaposition of the first and second zones 82 and 104 places this uniform perfusion of WB adjacent to the PRP collection region 76 and in a plane that is approximately the same as the plane in which the preferred, controlled position of the interface 58 lies. Once beyond the constricted passage 108 of the zone dam 104, the RBC 96 rapidly move toward the high-G wall 24 in response to centrifugal force.

The constricted passage 108 of the zone dam 104 brings WB into the entry region 74 at approximately the preferred, controlled height of the interface 58. WB brought into the entry region 74 below or above the controlled height of the interface 58 will immediately seek the interface height and, in so doing, oscillate about it, causing unwanted secondary flows and perturbations along the interface 58. By bringing the WB into the entry region 74 approximately at interface level, the zone dam 104 reduces the incidence of secondary flows and perturbations along the interface 58.

The juxtaposed surface contours of the high-G and low-G walls 24 and 26 further create a third dynamic flow zone 110 beyond the WB entry region 74 and the PRP collection region 76 of the first compartment 38. There (see FIGS. 8, 10 and 11), the surface 111 of the low-G wall 26 tapers outward away from the axis of rotation 28 toward the high-G wall 24 in the direction of WB flow. In this zone 110, the high-G wall surface 113 across from the surface 111 retains a constant radius.

This juxtaposition of contours along the high-G and low-G walls 24 and 26 produces a dynamic circumferential plasma flow condition generally transverse the centrifugal force field in the direction of the PRP collection region 76. The circumferential plasma flow condition in this direction continuously drags the interface 58 back toward the PRP collection region 76, where the higher radial plasma flow conditions already described exist to sweep even more platelets off the interface 58. Simultaneously, the counter-flow patterns serve to circulate the other heavier components of the interface 58 (the lymphocytes, monocytes, and granulocytes) back into the RBC mass, away from the PRP 98 stream.

The juxtaposed surface contours of the high-G and low-G walls 24 and 26 further create a fourth dynamic flow zone 112 in the RBC collection region 80 of the first compartment 38. There, the surface 115 of the low-G wall 26 steps radially toward the high-G wall 24, while the high-G wall 24 remains iso-radial. This juxtaposition of the high-G and low-G walls 24 and 26 creates a stepped-up barrier zone 112 in the RBC collection region 80. The stepped-up barrier zone 112 extends into the RBC mass along the high-G wall 24, creating a restricted passage 114 between it and the facing, iso-radial high-G wall 24 (see FIG. 8). The restricted passage 114 allows RBC 96 present along the high-G wall 24 to move beyond the barrier zone 112 for collection by the RBC collection passage 78. Simultaneously, the stepped-up barrier zone 112 blocks the passage of the PRP 98 beyond it, keeping the PRP 98 within the dynamic flow conditions created by the first, second, and third zones 82, 104, and 110.

As FIG. 3 shows, the dog leg portion 70 of the RBC collection passage 78 is also tapered. Due to the taper, the passage 78 presents a greater cross section in the RBC collection region 80. The taper of the dog leg portion 70 is preferably gauged relative to the taper of the low-G wall 26 in the third flow zone 110 to keep fluid resistance within the passage 78 relatively constant, while maximizing the available separation and collection areas outside the passage 78. The taper of the dog leg portion 70 also facilitates the removal of air from the passage 78 during priming.

SEPARATION IN THE SECOND PROCESSING COMPARTMENT

The second processing compartment 40 receives PRP 98 from the first processing compartment 38 through the port 56 (of which FIG. 20 shows an interior view). The PRP 98 separates in the centrifugal field within the second compartment 40 into platelet concentrate (PC, designated by numeral 116), which moves toward the high-G wall 24, and platelet-poor plasma (PPP, designated by numeral 118), which is displaced by the moving PC toward the low-G wall 26. The port 54 conveys PPP 118 from the second compartment 40. The PC 116 remains in the second compartment 40 for later resuspension and transport to an external storage container.

The second compartment 40 (see FIG. 3) includes a fifth interior seal 120 between the PRP inlet port 56 and the PPP collection port 54. The fifth seal 120 extends in a first region 122 generally parallel to the second seal 44 and then bends away in a dog-leg 124 in the direction of circumferential PRP flow within the second compartment 40. The dog-leg portion 124 terminates near the longitudinal side edge of the second compartment 40 opposite to the longitudinal side edge formed by the second interior seal 90.

The fifth interior seal 120, the second interior seal 90, and the lower regions of the first peripheral seal 42 together form a PPP collection passage 126. The PPP collection passage 1126 receives PPP at its open end and from there channels the PPP to the PPP collection port 54.

PRP enters the second compartment 40 in a PRP entry region 128 (see FIG. 20). The PRP enters the region 128 through the port 56 in an axial path. The PRP departs the region 128 in a circumferential path toward the opposite longitudinal side edge. This creates within the PRP entry region 128 a vortex flow pattern 130 (see FIG. 20), called a Taylor column. The vortex flow pattern 130 circulates about an axis 132 that is generally parallel to the rotational axis 28 and stretches from the outlet of the port 56 longitudinally across the circumferential flow path of the chamber 40. The vortex region flow pattern 130 perfuses the PPP into the desired circumferential flow path for separation into PC 116 and PPP 118 in a sixth flow zone 140 located beyond the PRP entry region 128.

In the illustrated and preferred embodiment, the surface of the low-G wall 26 is contoured to create a fifth dynamic flow zone 134 in the PRP entry region 128. The flow zone 134 controls the perfusion effects of the vortex flow pattern 130.

More particularly, in the fifth flow zone 134, the surface of the low-G wall 26 steps radially toward the high-G wall 24 to form a stepped-up ridge 136 in the PRP entry region 128 (see FIGS. 8; 13; and 20). In the fifth flow zone 134, the low-G wall then radially recedes away from the high-G wall 24 to form a tapered surface 138 leading from the ridge 136 in the direction of circumferential PRP flow. The high-G wall 24 remains iso-radial throughout the fifth flow zone 134, and the remainder of the second compartment 40.

The stepped up ridge 136 reduces the radial width of the PRP entry region 128. The reduced radial width reduces the strength of the vortex flow pattern 130, thus lowering the shear rate and subsequent shear stress on the platelets. The reduced radial width also reduces the time that platelets dwell in the vortex flow pattern 130. By both reducing shear stress and exposure time to such shear stress, the reduced radial width reduces the likelihood of damage to platelets.

The reduced radial width also creates a vortex flow pattern 130 that is more confined, compared to the flow pattern 130' with a less radially confined area, as FIG. 21 shows. The trailing tapered surface 138 also further directs the perfusion of PRP gently from the more confined vortex flow pattern 130 toward the low-G wall 26 and into the sixth flow zone 140. The results are a more effective separation of PC from the PRP in the sixth flow zone 140.

The sixth flow zone 140 has a greater radial width than the PRP entry region 128. This greater radial width is desirable, because it provides greater volume for actual separation to occur.

The radial width of the PRP entry region 128 is believed to be important to optimize the benefits of the vortex flow pattern 130 in separating PC from PRP. If the radial width is too large (as shown in FIG. 21), the resulting vortex flow pattern 130' is not well confined and more vigorous. Platelets are held longer in the flow pattern 130, while also being subjected to higher shear stress.

Figure 22:
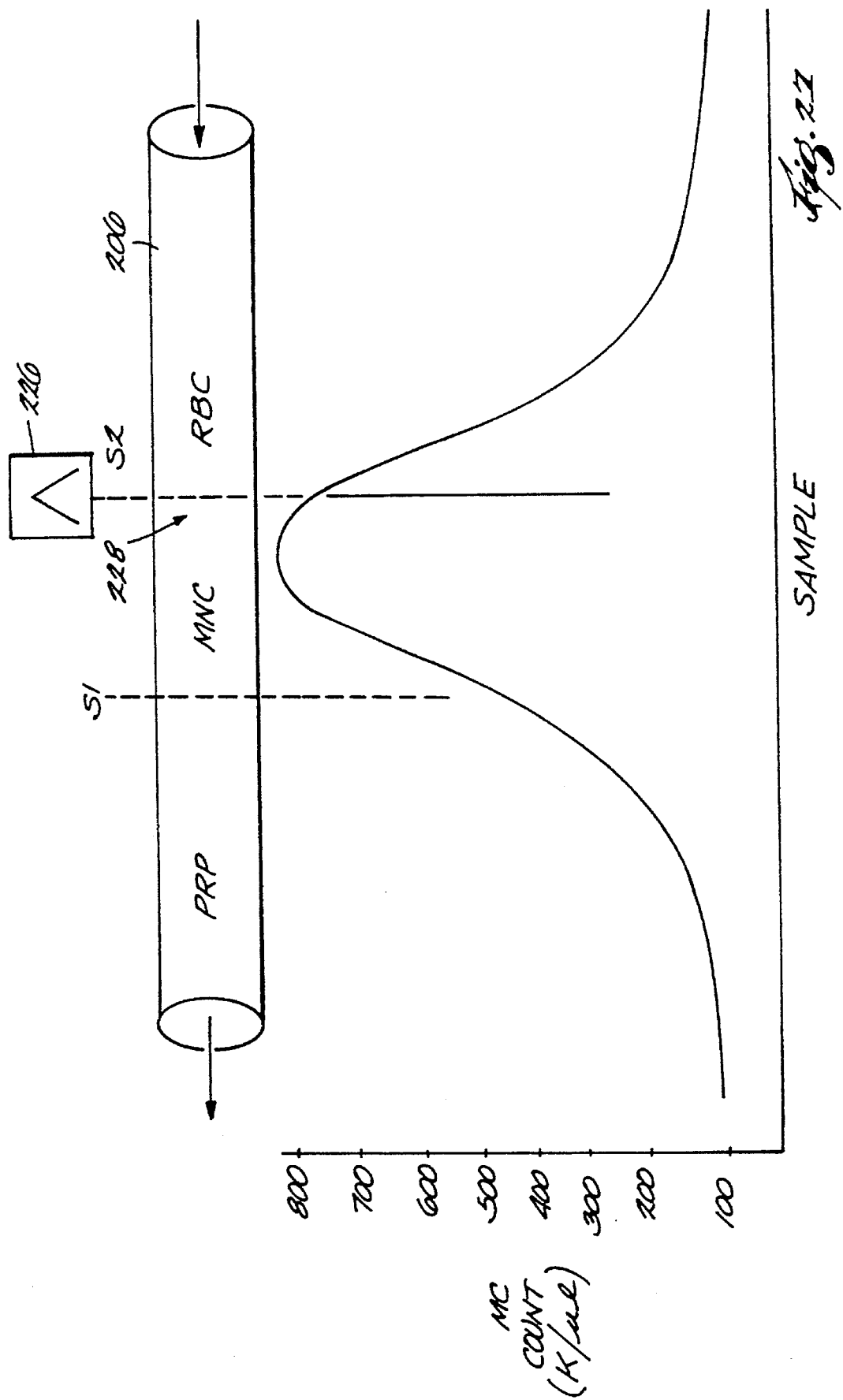

On the other hand, if the radial width of the PRP entry region 128 is too small (as FIG. 22 shows), the increasing flow resistance, which increases in cubic fashion as the radial width decreases, will cause the vortex pattern 130 to shift out of the region of small radial width into a region where a larger radial width and less flow resistance exists. Thus, the vortex flow pattern will not occur in the PRP entry region 128. Instead, the flow pattern 130" will form away from axial alignment with the PRP port 56, where a larger radial width, better conducive to vortex flow, is present. The effective length of the circumferential separation path is shortened, leading to reduce separation efficiencies.

Furthermore, the resulting, shifted vortex flow pattern 130 is likely not to be well confined and will thus subject the platelets to undesired shear stresses and dwell time.

The dimensionless parameter (λ) can be used to differentiate between a radial width that is too wide to provide well confined control of the vortex flow pattern 130 and reduced width that does. Disclosed in U.S. Pat. No. 5,316,667, the dimensionless parameter (λ) accurately characterizes the combined attributes of angular velocity, channel thickness or radial width, kinematic viscosity, and axial height of the channel, expressed as follows:

$$\lambda = \frac{(2\Omega h^3)}{(vZ)}$$

where:

Ω is the angular velocity (in rad/sec);

h is the radial depth (or thickness) of the chamber (in cm);

v is the kinematic viscosity of the fluid being separated (in cm$^2$/sec); and

Z is the axial height of the chamber (in cm).

It is believed that a reduced radial width in the PRP entry region 128 sufficient to provide a parameter ($\lambda$) $\leq$100 will promote the desired confined vortex flow conditions shown in FIG. 20. A parameter ($\lambda$) of about 40 to 50 is preferred. Due to a larger radial width in the sixth flow zone 140 (realizing that the angular velocity and the kinematic viscosity of the PRP being separated remain essentially the same) the parameter ($\lambda$) will be significantly larger in the sixth flow zone 140. Parameters ($\lambda$) typically can be expected in the sixth flow zone 140 to be in the neighborhood of 500 and more.

It is believed that flow resistance, expressed as the change in pressure per unit flow rate, can be used to define the boundary at which a narrower radial width in the PRP entry region 128 causes shifting of the vortex flow pattern 130, as FIG. 22 shows. Empirical evidence suggests that vortex flow shifting will occur in the region 128 when flow resistance in the vortex reaches about 90 dyne sec/cm$^4$, which is equivalent to the flow resistance plasma encounters flowing at 30 ml/min in a space that is 0.1 cm wide, 1.0 cm long, and 5.0 cm high, while being rotated at 3280 RPM.

The juxtaposed surface contours of the high-G and low-G walls 24 and 26 further create the sixth dynamic flow zone 140 beyond the PRP entry region 128 of the second compartment 40. Here, the surface 141 of the low-G wall 26 tapers outward away from the axis of rotation 28 toward the high-G wall 24 in the direction of perfused PRP flow in the second compartment 40. In this zone 140, the high-G wall 24 retains a constant radius.

The tapered low-G wall 26 in the sixth flow zone 140 provides a greater radial width where a substantial majority of PC separation occurs. Typically, most of PC separation occurs in the first half segment of the sixth flow zone 140. The PC deposit along the high-G wall 24 in great amounts in this half-segment of the sixth flow zone 140, creating a layer along the high-G wall 24 in this half-segment as much as 1 mm in thickness. The greater radial width in this half-segment of the sixth flow zone accommodates the concentrated volume of PC without adversely reducing the necessary separation volume.

In the illustrated and preferred embodiment, the dog-leg portion 124 of the associated PPP collection passage 126 is tapered.

As with the taper of the dog leg portion 70, the taper of the dog-leg portion 124 is preferably gauged relative to the taper of the low-G wall 26 to keep fluid resistance within the PPP collection passage 126 relatively constant. The taper also facilitates the removal of air from the passage 126 during priming.

As FIGS. 8 and 10 best shows, the surface 142 of the low-G wall 26 of the spool element 18 between the first flow zone 82 (in the first compartment 38) and the fifth flow zone 134 (in the second compartment 40) tapers away from the high-G wall 24 in the direction from the fifth zone 134 toward the first zone 82. The radial facing surface of the high-G wall 24 remains iso-radial. The portion of the PPP collection passage 126 axially aligned with the PPP collection port 54 (in the second compartment 140) and the portion of the RBC collection passage 78 axially aligned with the RBC collection port 52 (in the first compartment 38) are carried between this low-G surfaces 142 and the opposed high-G wall. The surface 142 provides a smooth transition between the PRP entry region 128 and the WB entry region 74.

Figure 23:
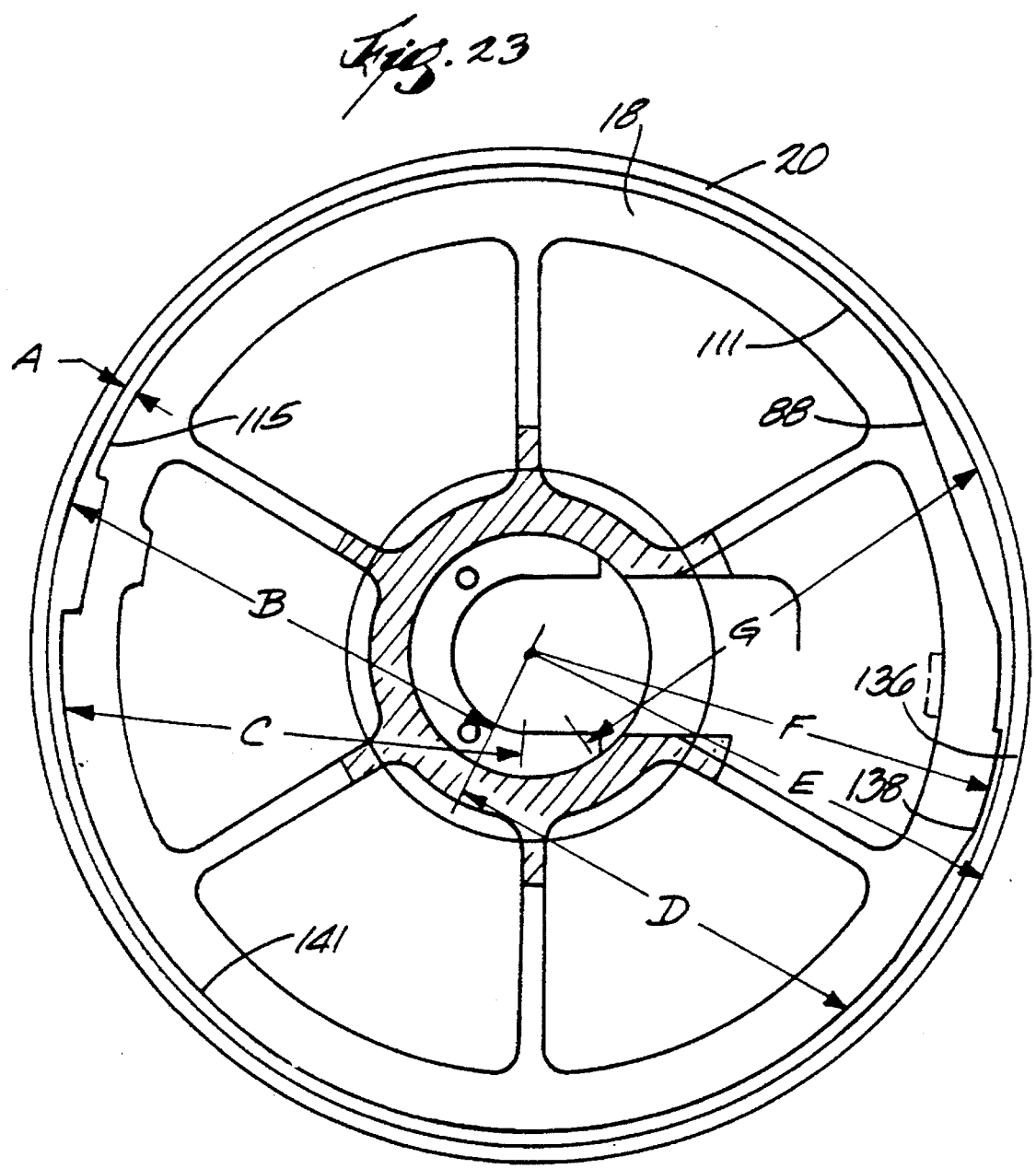
FIG. 23 is a top view of a bowl element and a spool element that embody features of the invention showing radii to major surface regions defined circumferentially on them.

FIG. 23 shows radii A to G for the principal surface regions described above along the spool element 18 and the bowl element 20. The following table lists the dimensions of these radii in a preferred implementation:

| Radii | Dimension (inches) |
| --- | --- |
| A | 0.035 |
| B | 3.062 |
| C | 3.068 |
| D | 2.979 |
| E | 3.164 |
| F | 3.070 |
| G | 2.969 |

The axial height of the surfaces in the preferred implementation is 3.203 inches.

In a preferred implementation (see FIG. 14), the surface 84 projects from the high-G wall for a distance (dimension H in FIG. 14) of 0.268 inch. The circumferential length of the surface 84 (dimension I in FIG. 14) is 0.938 inch, and the length of the tapered surface 86 (dimension J in FIG. 14) is 0.343 inch. The angle of the tapered surface 86 is 29 degrees.

In a preferred implementation (see FIG. 9), the surface 106 projects from the high-G wall for a distance (dimension K in FIG. 9) of 0.103 inch. The circumferential length of the surface 106 (dimension L in FIG. 9) is 1.502 inches.

Collection of Mono Nuclear Cells (MNC)

The first processing compartment 38 as heretofore described (and as best exemplified in FIG. 3), when carried between the contoured low-G and high-G surfaces of the spool element 18 and bowl element 20 as heretofore described (and as best exemplified in FIGS. 7 to 11), can also be used to harvest MNC from whole blood.

Figure 24:
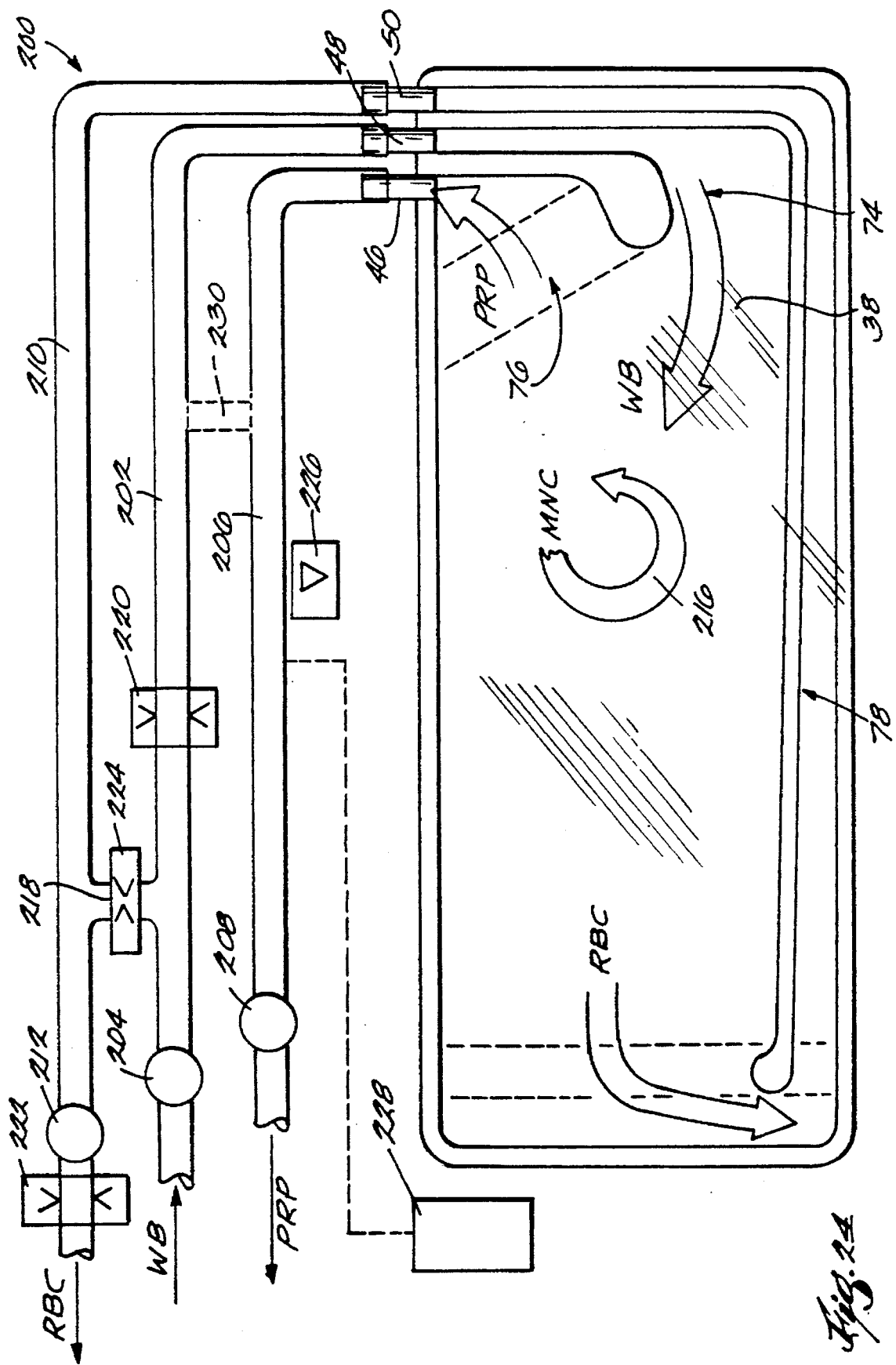
FIG. 24 shows a system for collecting mono nuclear cells (MNC), using the apparatus shown in the preceding figures, the system being shown in a whole blood processing mode.

FIG. 24 shows a system 200 that employs the first processing compartment 38 carried by the spool and bowl elements 18/20 for harvesting MNC, which for simplification are not show. The system 200 does not use the second processing compartment 40.

In this embodiment, whole blood from a donor is conveyed through inlet tubing 202 by inlet pump 204 through the port 48 into the WB entry region 74. During this time, the compartment 38 is rotated at about 3280 RPM. Whole blood separates into RBC and PRP within the compartment 38, as already described.

PRP is conveyed back to the donor through outlet tubing 206 by outlet pump 208. The outlet tubing 206 communicates with the PRP collection region 76 through the port 46, as already described. RBC, too, is conveyed back to the donor through outlet tubing 210 by outlet pump 212. The outlet tubing 210 communicates with the RBC collection passage 78 through the port 50, as already described.

In the preferred embodiment, the conveyance of WB from the donor into the separation compartment 38 occurs essentially simultaneously with the return of PRP and RBC to the donor. Still, it should be appreciated that a single needle batch technique with successive draw and return cycles could also be used.

Figure 25:
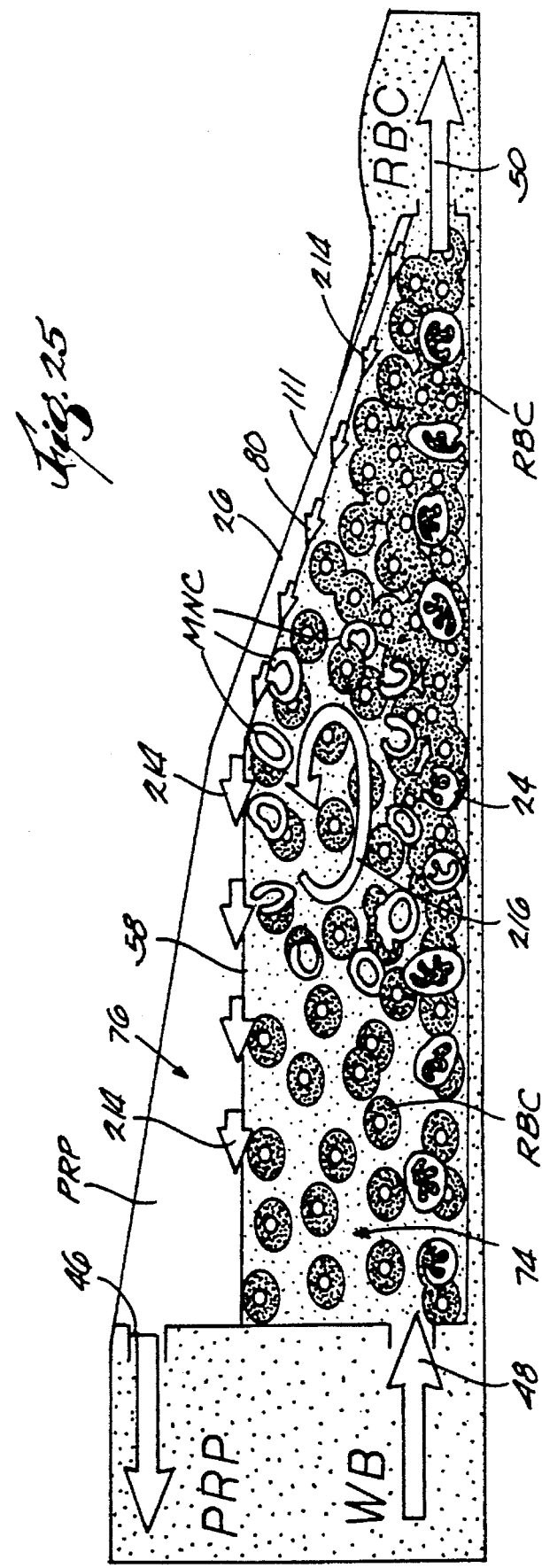
FIG. 25 is a diagrammatic view showing the dynamic flow conditions established that confine and "park" the MNC during the whole blood processing mode shown in FIG. 24.

As also previously described in the context of a platelet collection procedure, a dynamic circumferential plasma flow condition develops in the compartment 38 generally transverse the centrifugal force field in the direction of the PRP collection region 76. FIG. 25 diagrammatically shows this dynamic plasma flow condition. MNC (designated as such in FIG. 25) initially settle along the high-G wall 24, but eventually float up to the surface of the interface 58 near the high-hematocrit RBC collection region 80

Figure 11:
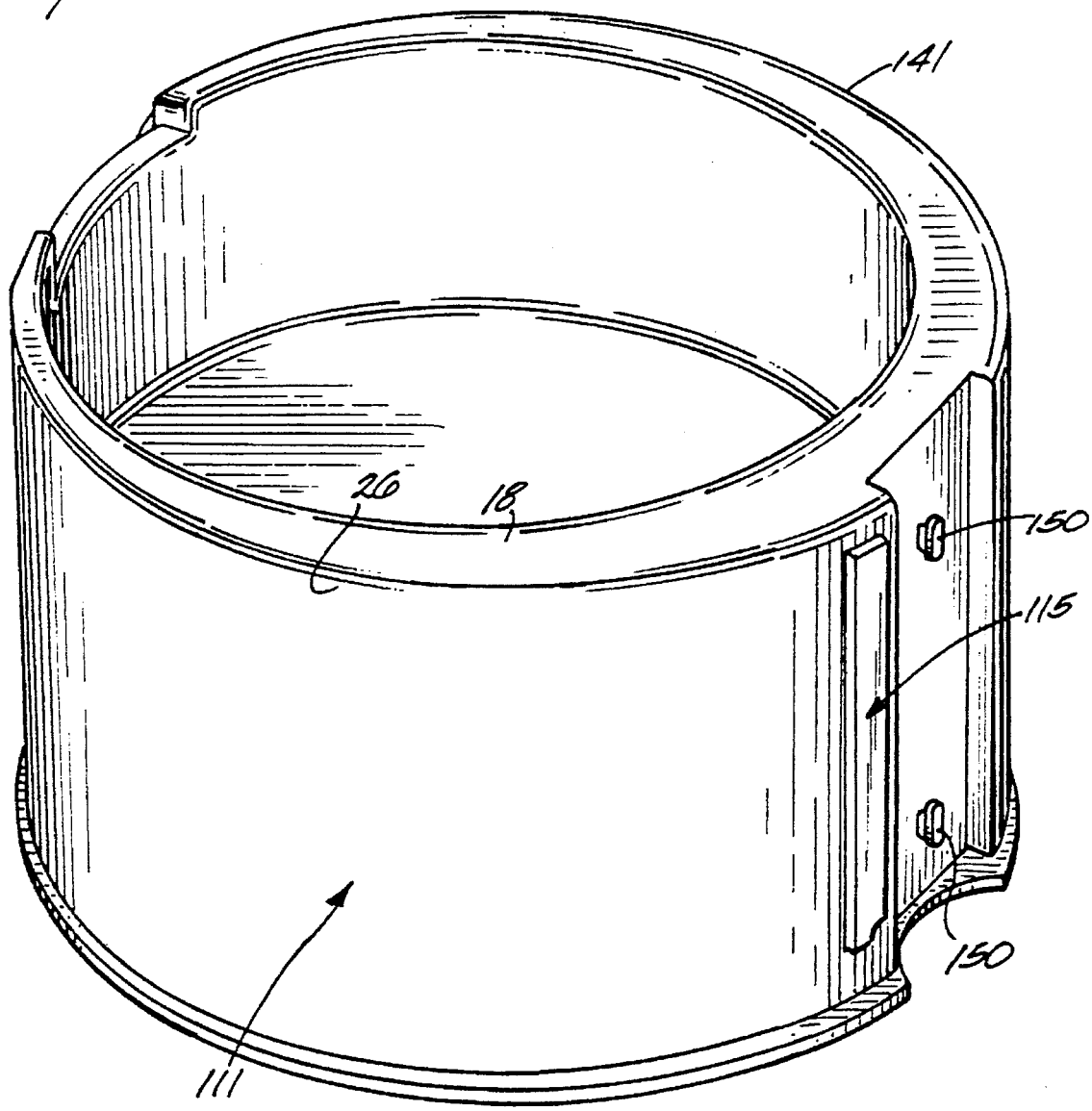
Figure 12:
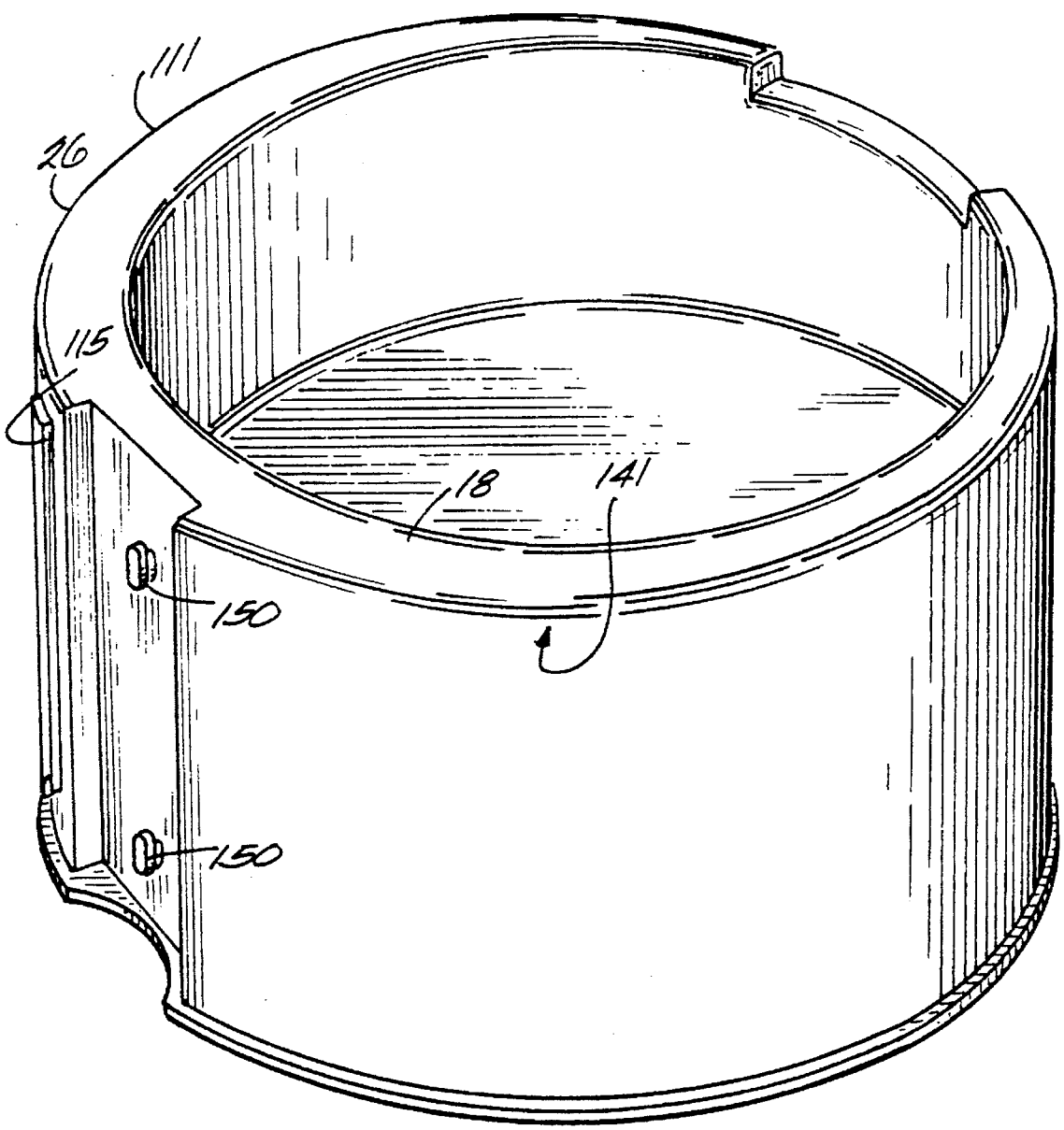

As described earlier, the low-G wall 26 (more specifically, the surface 111, as shown in FIG. 8, 10, and 11) is tapered outwardly toward the high-G wall 24 in the direction of WB flow, while the high-G wall remains iso-radial. This juxtaposition of contours creates the plasma counterflow patterns, shown by arrows 214 in FIG. 25. These counterflow patterns 214 draw the MNC back toward the low-hematocrit PRP collection region 76. MNC again resettle near the low-hematocrit PRP collection region 76 toward the high-G wall 24.

The MNC circulate in this path, designated 216 in FIG. 25, while WB is separated into RBC and PRP. The MNC are thus collected and "parked" in this confined path 216 within the compartment 38 away from both the RBC collection region 50 and the PRP collection region 76.

Figure 26:
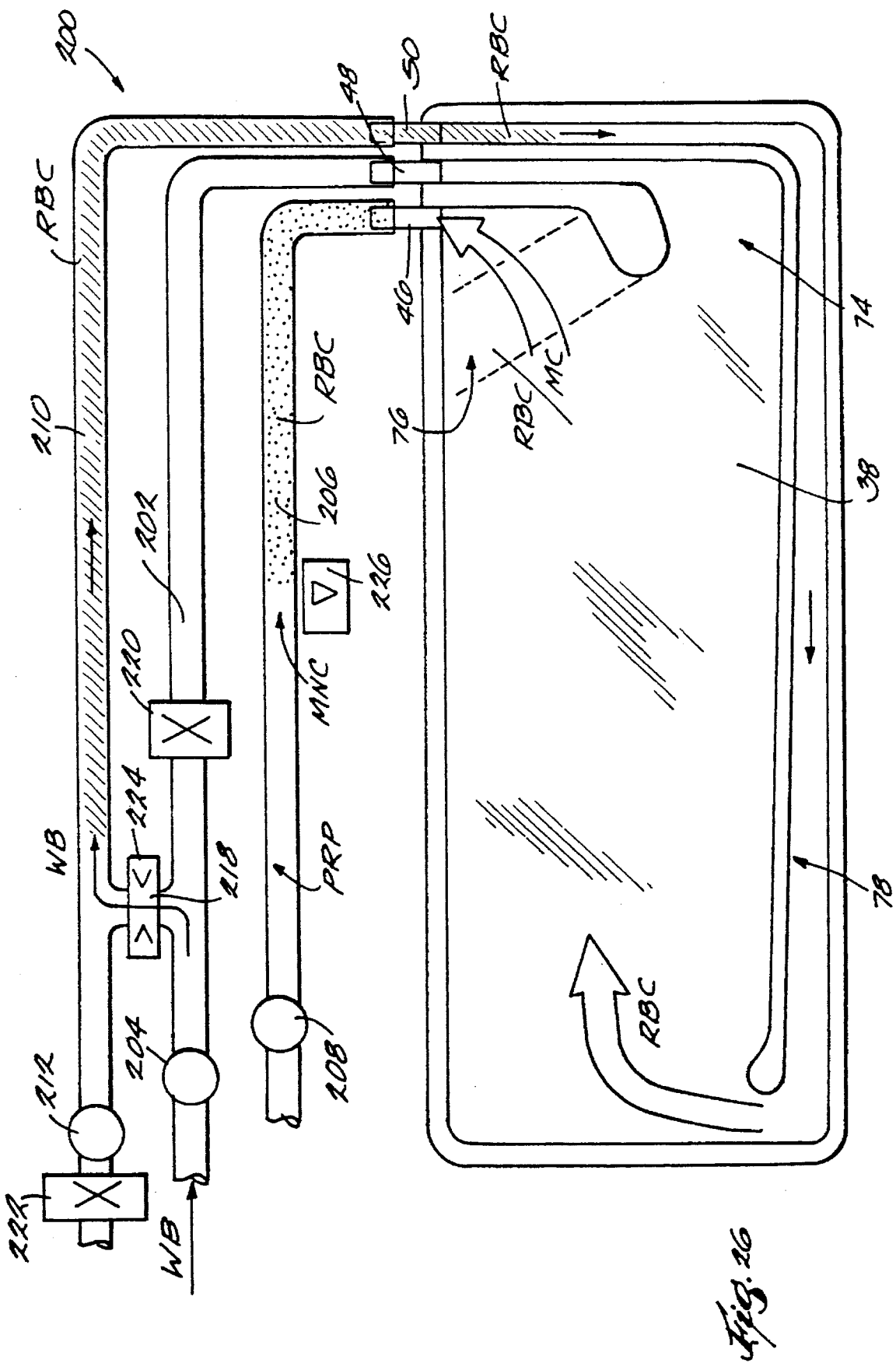
FIG. 26 shows the system of FIG. 24 in a reverse flow mode, to expel the MNC for collection.

After a prescribed processing interval (see FIG. 26), the system 200 redirects the WB from the donor through a branch path 218 between the WB inlet tubing 202 and the RBC outlet tubing 210. A clamp 220 closes the WB inlet tubing 202 downstream of the branch path 218 (FIG. 24 shows this clamp 220 opened during the preceding WB separation stage). A clamp 222 also closes the RBC outlet tubing 210 downstream of the branch path 218 (FIG. 24 also shows this clamp 222 opened during the preceding WB separation step), and the RBC pump 212 is halted. A clamp 224 opens the branch path 218 (as FIG. 26 shows) and closes the branch path 218 (as FIG. 24 shows)

As a result, WB flows through the RBC outlet tubing 210 in a flow direction opposite to the preceding RBC flow to the donor. The WB displaces RBC in the outlet tubing 210 back into the compartment 38 in a reverse flow direction through the port 50 and RBC collection passage 78, while rotation of the compartment 38 continues.

The reverse flow of RBC into the compartment 38 increases hematocrit in the PRP collection region 76, causing the MNC to float back to the surface of the interface 58. The interface 58, and with it, the MNC are expelled by the reverse RBC flow through the PRP collection port 46 and into the outlet tubing 206.

An in-line sensor 226 in the outlet tubing 206 senses the presence of RBC. Upon sensing RBC, the sensor 226 sends a command signal to stop the WB inlet pump 204 and, accordingly, the back flow of RBC through the compartment 38.

As FIG. 27 shows, the population of MNC is significantly concentrated in the interface region 228 immediately next to the RBC, which is what the sensor 226 detects. To complete the collection precess, the operator heat seals the outlet tubing 206 (shown as S1 and S2 in FIG. 27) on opposite sides of this region 228 to capture the concentrated population of MNC for further off-line processing.

In an alternative embodiment, the system 200 can include a PRP recirculation path (shown in phantom lines as 230 in FIG. 24) to recirculate a portion of the PRP for mixing with WB entering the compartment 38. In this way, the system 200 controls the entry hematocrit. The system 200 can also open the clamp 224 to recirculate a portion of RBC through the branch path 218 for mixing with WB entering the compartment to control exit hematocrit. By controlling entry and exit hematocrits, the operator can control the location of the MNC path 216 during WB processing. In a preferred embodiment, a separate collection container 228 can be coupled to outlet tubing 206 to receive multiple aliquots of MNC separated during sequential processing steps where the MNC are just parked within the separation compartment 38 (as shown in FIG. 34) and then harvested by RBC backflow (as shown in FIG. 26). Container 228 could also receive a single aliquot of MNC instead of sealing the MNC in the tubing 206.

Pre-clinical tests have demonstrated the ability of the system 200 just described to harvest $5.7 \times 10^9$ MNC out of a total precount of $6.7 \times 18$ MNC, for an efficiency of 85.1%. Subsequent antigen studies reveal the presence of stem cells in the MNC collected.

Various features of the inventions are set forth in the following claims.

We claim:

1. A blood separation system comprising a chamber for rotation about a rotational axis comprising first and second spaced apart walls forming a separation zone having a low-G side located closer to the rotational axis than the other, high-G side, the separation zone including an inlet region where whole blood enters the separation zone for separation into red blood cells, a plasma constituent carrying platelets, and an interface carrying mono nuclear cells between the red blood cells and plasma constituent, and an exit region spaced from the inlet region where red blood cells collect during separation, and a controller operable in a first mode to convey whole blood into the inlet region for flow toward the exit region while removing red blood cells and the plasma constituent from the chamber and while retaining the interface substantially within the chamber, the controller further operable in a second mode to backflow red blood cells into the exit region for back flow toward the inlet region while removing the interface from the chamber.

2. A system according to claim 1 wherein at least a portion of the low-G side between the inlet and exit regions is displaced radially into the separation zone toward the high-G side in the direction of whole blood flow.

3. A system according to claim 1 or 2 and further including a flow restricting dam on the high-G side that restricts flow of whole blood in the inlet region to a reduced passage.

4. A system according to claim 3 wherein the interface is located in a plane within the chamber, and wherein the reduced passage directs the flow of whole blood in the inlet region in a plane essentially aligned with the plane of the interface.

5. A blood separation system comprising a chamber for rotation about a rotational axis to separate whole blood into red blood cells, a plasma constituent carrying platelets, and an interface carrying mono nuclear cells between the red blood cells and plasma constituent, the chamber comprising first and second spaced apart walls forming a separation zone having a low-G side located closer to the rotational axis than the other, high-G side, the separation zone including an inlet region where whole blood enters the separation zone to begin separation into red blood cells toward the high-G side and the plasma constituent toward the low-G side and a second region spaced from the inlet region, a first port communicating with the low-G side of the inlet region for collecting the plasma constituent in the inlet region of the separation zone, a second port communicating with the high-G side of the second region for collecting red blood cells in the second region of the separation zone, and a controller operable in a first mode to conduct whole blood into the inlet region of the chamber in a first flow direction toward the second region while collecting red blood cells through the second port and plasma constituent through the first port, and in a second mode to back flow red blood cells through the second port into the second region in a second flow direction toward the inlet region while collecting the interface through the first port.

6. A blood separation system comprising a chamber for rotation about a rotational axis to separate whole blood into red blood cells, a plasma constituent carrying platelets, and an interface carrying mono nuclear cells between the red blood cells and plasma constituent, the chamber comprising first and second spaced apart walls forming a separation zone having a low-G side located closer to the rotational axis than the other, high-G side, the separation zone including an inlet region having a radial width where whole blood enters the separation zone to begin separation into red blood cells toward the high-G side and the plasma constituent toward the low-G side and a second region having a radial width spaced from the inlet region, a first port communicating with the low-G side of the inlet region for collecting the plasma constituent in the inlet region of the separation zone, a second port communicating with the high-G side of the second region for collecting red blood cells in the second region of the separation zone, the low-g side including a portion extending toward the second region that is displaced radially into the separation zone toward the high-g side, thereby reducing the radial width of the second region compared to the radial width of the inlet region, and a controller operable in a first mode to conduct whole blood into the inlet region of the chamber in a first flow direction toward the second region while collecting red blood cells through the second port and plasma constituent through the first port, and in a second mode to back flow red blood cells through the second port into the second region in a second flow direction toward the inlet region while collecting the interface through the first port.

7. A system according to claim 5 or 6 and further including a flow restricting dam on the high-G side that restricts flow of whole blood in the inlet region to a reduced passage.

8. A system according to claim 7 wherein the interface is located in a plane within the chamber, and wherein the reduced passage directs the flow of whole blood in the inlet region in a plane essentially aligned with the plane of the interface.

9. A method for separating mono nuclear cells from whole blood comprising the steps of rotating a separation chamber about a rotational axis, introducing whole blood into a first region of the chamber during its rotation to separate the whole blood into a plasma constituent, red blood cells, and an interface between the red blood cells and the plasma constituent, the interface containing mono nuclear cells, while conveying whole blood into the first region, collecting the plasma constituent in the first region, while conveying whole blood into the first region, collecting the red blood cells in a second region of the chamber spaced from the first region, thereafter backflowing red blood cells into the second region in a back flow direction toward the first region, and while backflowing red blood cells into the second region, collecting the interface in the first region.

10. A method according to claim 9 and further including the step, conducted while backflowing whole blood into the first inlet region, of creating a back flow of plasma constituent along the interface from the second region toward the first region to maintain a high-relative hematocrit in the second region and a low-relative hematocrit in the first inlet region, whereby the mono nuclear cells are confined between the low-relative hematocrit first region and the high-relative second region while whole blood is conveyed into the first region.

11. A method according to claim 9 wherein rotation of the chamber creates a low-G wall radially close to the axis and a high-G wall spaced radially further from the axis than the low-G wall, wherein, during the step of collecting the plasma constituent, the plasma constituent is directed through a reduced passage on the low-G wall to an outlet in the first region for transport from the chamber.

12. A method according to claim 11 wherein, during the step of conveying whole blood into the inlet region, the whole blood is directed through a reduced passage.

13. A method according to claim 11 wherein the interface in the first region lies in a plane, and wherein in conveying the whole blood into the first region, the whole blood is conveyed through a restricted passage in a plane that is essentially aligned with the plane of the interface.

* * * * *

UNITED STATES PATENT AND TRADEMARK OFFICE
CERTIFICATE OF CORRECTION

PATENT NO.   :   5,573,678

DATED        :   November 12, 1996

INVENTOR(S)  :   Richard I. Brown et al.

It is certified that error appears in the above-identified patent and that said Letters Patent is hereby corrected as shown below:

| | |
|---|---|
| Column 2, Line 55 | After "high-G" delete "G" |
| Column 9, Line 48 | Delete "1126" and substitute --- 126 --- |
| Column 11, Line 61 | Delete "140" and substitute --- 40 --- |
| Column 13, Line 51 | Delete "precess" and substitute --- process --- |
| Column 16, Line 26 | Delete "inlet" |
| Column 16, Line 30 | Delete "inlet" |

Signed and Sealed this

Second Day of June, 1998

Attest:

BRUCE LEHMAN

Attesting Officer

Commissioner of Patents and Trademarks